(12) United States Patent
Lau

(10) Patent No.: US 8,784,627 B2
(45) Date of Patent: Jul. 22, 2014

(54) GRAFT COPOLYMERS, THEIR PREPARATION AND USE IN CAPILLARY ELECTROPHORESIS

(75) Inventor: Aldrich N. Lau, Palo Alto, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1148 days.

(21) Appl. No.: 12/565,590

(22) Filed: Sep. 23, 2009

(65) Prior Publication Data

US 2010/0187111 A1      Jul. 29, 2010

Related U.S. Application Data

(63) Continuation of application No. 10/629,524, filed on Jul. 29, 2003, now abandoned.

(60) Provisional application No. 60/399,662, filed on Jul. 29, 2002, provisional application No. 60/399,663, filed on Jul. 29, 2002.

(51) Int. Cl.
*G01N 27/447* (2006.01)

(52) U.S. Cl.
USPC .......................................... 204/455; 204/469

(58) Field of Classification Search
USPC ................... 204/469, 605, 606, 456, 455
See application file for complete search history.

(56) References Cited

U.S. PATENT DOCUMENTS

| | | | | |
|---|---|---|---|---|
| 2,620,324 | A | 12/1952 | Coover | 260/45.5 |
| 2,899,405 | A | 8/1959 | Coover et al. | 260/45.5 |
| 3,826,678 | A | 7/1974 | Hoffman et al. | 117/81 |
| 4,548,498 | A | 10/1985 | Folestad et al. | 356/318 |
| 4,675,300 | A | 6/1987 | Zare et al. | 436/172 |
| 4,865,707 | A | 9/1989 | Karger et al. | |
| 4,908,112 | A | 3/1990 | Pace | 204/299 R |
| 4,997,537 | A | 3/1991 | Karger et al. | 204/182.8 |
| 5,126,021 | A | 6/1992 | Grossman | 204/180.1 |
| 5,192,412 | A | 3/1993 | Kambara et al. | 204/299 R |
| 5,344,455 | A | 9/1994 | Keogh et al. | 623/11 |
| 5,384,024 | A | 1/1995 | Moring et al. | 204/299 R |
| 5,468,365 | A | 11/1995 | Menchen et al. | 204/299 R |
| 5,530,069 | A | 6/1996 | Neff et al. | 525/329.4 |
| 5,552,028 | A | 9/1996 | Madabhushi et al. | 204/451 |
| 5,916,426 | A | 6/1999 | Madabhushi et al. | 204/451 |
| 5,929,173 | A | 7/1999 | Midha et al. | 525/301 |

(Continued)

FOREIGN PATENT DOCUMENTS

| | | |
|---|---|---|
| EP | 1 295 113 B1 | 7/2006 |
| GB | 824263 | 11/1959 |

(Continued)

OTHER PUBLICATIONS

International Search Report for PCT/US03/23457, Oct. 27, 2003.

(Continued)

*Primary Examiner* — Alex Noguerola

(57) ABSTRACT

The invention relates to graft copolymers, their preparation, and compositions, such as electrophoresis separation media, containing the same; also to ultra-high molecular weight poly (N,N-dimethylacrylamide) ("poly(DMA)") polymers, their preparation, and compositions, such as electrophoresis separation media, containing the same; and more particularly to supports, such as capillaries, containing these polymers and methods for separating biomolecules, especially polynucleotides, using capillary electrophoresis. The graft copolymers can be prepared by, e.g., grafting polyacrylamide units onto a poly(DMA) backbone. Separation media comprising such graft copolymers or ultra-high molecular weight poly(DMA) polymers yield superior performance in the analysis and separation of biomolecules by capillary electrophoresis.

29 Claims, 1 Drawing Sheet

Figure 1: Performance of IC3 in CE DNA sequencing

(56) References Cited

U.S. PATENT DOCUMENTS

| | | | |
|---|---|---|---|
| 5,945,319 A | 8/1999 | Keogh | 435/174 |
| 5,955,557 A | 9/1999 | Machida et al. | 526/346 |
| 6,100,338 A | 8/2000 | Akashi et al. | 525/212 |
| 6,124,396 A | 9/2000 | Hahn et al. | 524/801 |
| 6,165,457 A | 12/2000 | Midha et al. | 424/78.17 |
| 6,214,958 B1 | 4/2001 | Le-Khac et al. | 526/318.3 |
| 6,319,976 B1 | 11/2001 | DeNicola, Jr. et al. | 524/504 |
| 6,537,432 B1 | 3/2003 | Schneider et al. | 204/450 |
| 6,716,948 B1 | 4/2004 | Klaerner et al. | 526/303.1 |
| 6,770,698 B1 | 8/2004 | Chu et al. | |
| 2001/0023827 A1 | 9/2001 | Liu et al. | |
| 2002/0029968 A1 | 3/2002 | Tan et al. | 204/454 |
| 2008/0257733 A1 | 10/2008 | Viovy et al. | |

FOREIGN PATENT DOCUMENTS

| | | |
|---|---|---|
| JP | 3032729 | 2/1991 |
| JP | 5080276 | 4/1993 |
| JP | 8253519 | 10/1996 |
| JP | 9020648 | 1/1997 |
| JP | 9236580 | 9/1997 |
| JP | 11174611 | 7/1999 |
| JP | 11265039 | 9/1999 |
| JP | 2000061275 | 2/2000 |
| WO | WO 00/42423 | 7/2000 |
| WO | WO 02/24313 | 3/2002 |
| WO | WO 02/101375 | 12/2002 |

OTHER PUBLICATIONS

"Standard Practice for General Techniques of Liquid Chromatography-Infrared (LC/IR) and Size Exclusion Chromatography-Infrared (SEC/IR) Analyses," ASTM Designation: E2106-00:1-7 (2000).

Adler, "Cross-linking of Polymers by Radiation," Science, 141(3578):321-29 (Jul. 26, 1963).

Albarghouthi et al., "Polymeric Matrices for DNA Sequencing by Capillary Electrophoresis," Electrophoresis 21:4096-4111 (Jul. 5, 2000).

Bae et al., "Polymeric Separation Media for Electrophoresis: Cross-Linked Systems or Entangled Solutions," Journal of Chromatography A, 652:17-22 (1993).

Barbier et al., "Comb-Like Copolymers as Self-Coating, Low-Viscosity and High-Resolution Matrices for DNA Sequencing," Electrophoresis 23:1441-1449 (2002).

Barton et al., "Radical Polymerization in Disperse Systems," Ellis Horwood, pp. 186-215 (1994).

Bode, "The Use of Liquid Polyacrylamide in Electrophoresis I. Mixed Gels Composed of Agar-Agar and Liquid Polyacrylamide" Anal. Biochem., 83:204-2010 (1977).

Bode, "The Use of Liquid Polyacrylamide in Electrophoresis II. Relationship Between Gel Viscosity and Molecular Sieving," Anal. Biochem., 83:364-371 (1977).

Bode, "The Use of Liquid Polyacrylamide in Electrophoresis III. Properties of Liquid Polyacrylamide in the Presence of Cellulose Acetate," Anal. Biochem., 92:99-110 (1979).

Burlant et al., "Block and Graft Polymers," Reinhold Publishing corporation, pp. 20-22, 31, 57-58, 94 (Oct. 1960).

Candau et al., "Kinetic Study of the Polymerization of Acrylamide in Inverse Microemulsion," Journal of Polymer Science, Polymer Chemistry Edition, 23:193-214 (1985).

Ceresa, "Block and Graft Copolymers," The National College of Rubber Technology, pp. 17, 29, 119, 128, 133, 180 (1962).

Costello et al., "Copolymers," Kirk-Othmer Encyc. of Chem. Technol., $4^{th}$ Ed., John Wiley & Sons, New York, vol. 7, pp. 349-381 (1993).

Cutler et al., "Chemical Characterization of Antiwear Films Generated by Tris-[p(perfluoroalkylether)phenyl] Phosphine Using X-ray Absorption Spectroscopy," Wear 236:165-78 (1999).

Drossman et al., "High-Speed Separations of DNA Sequencing Reactions by Capillary Electrophoresis," Anal. Chem., 62:900-903 (1990).

Engelhardt et al., "Preparation and Stability Tests for Polyacrylamide-Coated Capillaries for Capillary Electrophoresis," Journal of Chromatography A, 716:27-33 (1995).

Faust, "Initiators (Cationic)," Kirk-Othmer Encyc. of Chem. Technol., $4^{th}$ Ed., John Wiley & Sons, New York, vol. 14, pp. 476-482 (1995).

Friberg et al., "Emulsions," Kirk-Othmer Encyc. of Chem. Technol., $4^{th}$ Ed., John Wiley & Sons, New York, vol. 9, pp. 393-413 (1979).

Gan et al., "Tunable Swelling Kinetics in Core-Shell Hydrogel Nanoparticles," Am. Chem. Soc. , 123:7511-7517 (Mar. 6, 2001).

Garfin, "Electrophoretic Methods," Introduction to Biophysical Methods for Protein and Nucleic Acid Research, Department of Biochemistry, University of Connecticut Health Center, Academic Press, pp. 53-54, 100-104 (1995).

Hamada, "Rotational Isomeric State Study of Molecular Dimensions and Elasticity of Perfluoropolyethers: Differences Between Demnum-, Fomblin-, and Krytox-type Main Chains," Phys. Chem. Chem. Phys., 2:115-22 (Sep. 1999).

Harrison et al., "Micromachining a Miniaturized Capillary Electrophoresis-Based Chemical Analysis System on a Chip," Science, 261:895-97 (1993).

Hjertén et al., "High-Performance Electrophoresis of Acidic and Basic Low-Molecular-Weight Compounds and of Proteins in the Presence of Polymers and Neutral Surfactants," J. Liquid Chromatography, 12:2471-77 (1989).

Hocking et al., "Water-Soluble Acrylamide Copolymers. VI. Preparation and Characterization of Poly[N,N-dimethylacrylamide-co-acrylamide] and Control Polyacrylamides," Journal of Polymer Science, Part A: Polymer Chemistry, 38:3128-45 (Jul. 18, 2000).

Huang et al., "DNA Sequencing Using Capillary Array Electrophoresis," Anal. Chem., 64:2149-2154 (1992).

Ito et al., "Research and Development of Bearings for Special Environments," Motion & Control (4):13-21 (1998).

Juranicŏvá et al, "Inverse Microemulsion Polymerization of Acrylamide in the Presence of N,N-Dimethylacrylamide," Die Angewandte Makromolekulare Chemie 258(Nr. 4502):27-31 (1998).

Kaneko et al., "Synthesis and Swelling-Deswelling Kinetics of Poly (N-isopropylacrylamide) Hydrogels Grafted with LCST Modulated Polymers," J. Biomater. Sci. Polymer Ed. 10(11):1079-91 (Jun. 8, 1999).

Karis et al., "Rheology of Perfluoropolyethers with Polar End Groups," The Society of Rheology: $72^{nd}$ Annual Meeting, Feb. 2001, Paper CG3 (Abstract) at http://www.rheology.org/sort012/abstract.

Klimchuk et al., "Water-Soluble Acrylamide Copolymers. IX. Preparation and Characterization of the Cationic Derivatives of Poly(acrylamide-co-N,N-dimethylacrylamide), Poly(acrylamide-co-methacrylamide), and Poly(acrylamide-co-N-t-butylacrylamide)," J. Polym. Sci. Polym. Chem. 39(14):2525-2535 (2001).

Lee et al., "Preparation of Surface-Modified Stimuli-Responsive Polymeric Membranes by Plasma and Ultraviolet Grafting Methods and Their Riboflavin Permeation," Polymer 36(1):81-85 (1995).

Liang et al., "Formation of Concentration Gradient and its Application to DNA Capillary Electrophoresis," Electrophoresis, 21:3600-08 (2000).

Lipp et al., "Acrylamide," Kirk-Othmer Encyc. of Chem. Technol. $4^{th}$ Ed., vol. 1, pp. 255-287, John Wiley & Sons, New York (1991).

Liu et al., "Optimization of High-Speed DNA Sequencing on Microfabricated Capillary Electrophoresis Channels," Anal. Chem., 71:566-73 (1999).

Lynn, Jr. et al., "Surfactants," Kirk-Othmer Encyc. of Chem. Technol., $4^{th}$ Ed., John Wiley & Sons, New York, vol. 23, pp. 478-541 (1997).

McGinniss, "Radiation Curing," Kirk-Othmer Encyc. of Chem. Technol., $4^{th}$ Ed., vol. 20, pp. 831-859, John Wiley & Sons, New York, 1996.

Odian, Principles of Polymerization, pp. 366, 633, McGraw-Hill Book Co., New York, (1970).

Perry, "Petroleum and Complex-Mixture Distillation," Perry's Chemical Engineer's Handbook, $6^{th}$ Ed., pp. 1371-1381 (1984).

Pross et al, "The Inverse Emulsion Polymerization of Acrylamide with Pentaerythritolmyristate as Emulsifier 1. Experimental Studies," Polymer International 45:22-26 (1998).

(56) References Cited

OTHER PUBLICATIONS

Quesada et al., "Replaceable Polymers for DNA Sequencing by Capillary Electrophoresis," Methods in Molecular Biology, vol. 162: Capillary Electrophoresis of Nucleic Acids, vol. 1: Introduction to the Capillary Electrophoresis of Nucleic Acids, pp. 139-149 (2001).
Quesada, "Replaceable Polymers in DNA Sequencing by Capillary Electrophoresis," Current Opinion in Biotechnology, pp. 82-93 (1997).
Qui et al., "Graft Copolymerization of Acrylamide onto Poly (N-Para-Tolylacrylamides) Films Initiated by Ceric Ion," ACTA Polymerica Sinica, (5):321-326 (Oct. 1987) (w/ English Abstract).
Quirk et al., "Initiators (Anionic)," Kirk-Othmer Encyc. of Chem. Technol., 4$^{th}$ Ed., John Wiley & Sons, New York, 1995, vol. 14, pp. 461-476.
Sanchez et al., "Initiators (Free-Radical)," Kirk-Othmer Encyc. of Chem. Technol., 4$^{th}$ Ed., John Wiley & Sons, New York, 1995, vol. 14, pp. 431-460.
Sato et al., "Graft Copolymerization of Benzyl Methacrylate onto Poly(Acryloyi-L-Valine) Microspheres by Using the Photoreaction of Side Carboxyl Groups with Lead Tetraacetate," J. Macromol. Sc. Chem., A23(6):749-759 (1986).
Sato et al., "Long-Lived Polymer Radicals. III. Synthesis of Block Copolymer by the Reaction of Living Poly(N-Methylacrylamide) Radical with Some Vinyl Monomers," Journal of Polymer Science, Polymer Chemistry Edition, 21:819-28 (1983).
Sato et al., "Long-Lived Polymer Radicals. VI. Polymerization of N-Methylmethacrylamide with Formation of Living Propagating Radicals," Journal of Polymer Science, Polymer Chemistry Edition, 22:3921-32 (1984).
Schulz et al., "Copolymers," Kirk-Othmer Encyc. of Chem. Technol. 3$^{rd}$ Ed. vol. 6, John Wiley & Sons, New York, pp. 798-818 (1979).
Seiler et al., "Planar Glass Chips for Capillary Electrophoresis: Repetitive Sample Injection, Quantitation, and Separation Efficiency," Anal. Chem., 65:1481-88 (1993).
Sheppard et al., "Initiators," Kirk-Othmer Encyc. of Chem. Technol., 3$^{rd}$ Ed. vol. 13, John Wiley & Sons, New York, pp. 355, 367-373 (1981).
Smets et al., "Synthesis of Graft Copolymers," Journal of Polymer Science, vol. XXXIV:287-307 (1959).
Song et al., "DNA Sequencing by Capillary Electrophoresis Using Copolymers of Acrylamide and N,N-Dimethyl-acrylamide," Electrophoresis, (22):729-736 (2001).
Song et al., "DNA Sequencing by Capillary Electrophoresis Using Mixtures of Polyacrylamide and Poly(N,N-dimethylacrylamide)," Journal of Chromatography A, 915:231-39 (2001).
Stannett et al., "Polymerization by High-energy Radiation," Comprehensive Polymer Science, vol. 4, Chain Polymerization II, Pergamon Press, 317-336 (1989).
Sudor et al., "New Block-Copolymer Thermoassociating Matrices for DNA Sequencing: Effect of Molecular Structure on Rheology and Resolution," Electrophoresis 22:720-728 (2001).
Swerdlow et al., "Capillary Gel Electrophoresis for Rapid, High Resolution DNA Sequencing," Nucleic Acids Research, 18:1415-1419 (1990).
Takeuchi et al., "Microspheres Prepared with a Temperature-Responsive Macromonomer," Macromol. Chem. 194:551-58 (1993).
Tanaka et al., "Long-Lived Polymer Radicals $^{2a)}$," Makromol. Chem. 181:2421-31 (1980).
Thomas, "Acrylamide Polymers", Encyc. of Polymer Science and Technology, Plastics, Resins, Rubbers, Fibers, vol. 1., John Wiley & Sons, pp. 177-197 (1964).
Tietz et al., "Advances in DNA Electrophoresis in Polymer Solutions," Electrophoresis, 13:614-16 (1992).
Trossarelli et al., "Solution Properties of Poly (N,N-Dimethylacrylamide)," J. Polymer Sci., 57:445-52 (1962).
Ushakova et al., "Synthesis of Low Molecular Weight Poly (N-Acryloylmorpholine) End-Functionalized with Primary Amino Groups, and Its Use as Macromonomer for the Preparation of Poly(Amidoarnines)," Macromol. Chem. Phys. 196:2927-39 (1995).
Viovy et al., "Principles of Size-Based Separations in Polymer Solutions," Capillary Electrophoresis in Analytical Biotechnology, pp. 478-508.
Williams, "The Analysis of DNA Restriction Fragments and Polymerase Chain Reaction Products by Dynamic Sieving Electrophoresis," Methods, 4:227-232 (1992).
Woolley et al., "Ultra-High-Speed DNA Sequencing Using Capillary Electrophoresis Chips," Anal. Chem., 67:3676-80 (1995).
Wyatt, "Light Scattering and the Absolute Characterization of Macromolecules," Analytica Chimica Acta, 272:1-40 (1993).
Yau, "New Polymer Characterization Capabilities Using Size Exclusion Chromatography with On-Line Molecular Weight-Specific Detectors," Cherntracts-Macromolecular Chemistry 1(1):1-36 (Jan. 1990).
EP09016132.4, Extended European Search Report mailed on Mar. 24, 2010.
EP10009256.8, Extended European Search Report mailed on Dec. 6, 2010.
J-L Viovy et al., "Principles of Size-Based Separations in Polymer Solutions," in Capillary Electrophoresis in Analytical Biotechnology, CRC Series in Analytical Biotechnology, CRC Press, Chapter 11, pp. 478-508 (1996).
ES Wilks, "Polymer Nomenclature and Structure: A Comparison of Systems Used by CAS, IUPAC, MDL, and DuPont. 3. Comb/Graft, Cross-Linked, and Dendritic/Hyperconnected/Star Polymers," J. Chem. Inf. Comput. Sci. 37:209-223 (1997).
PCT/US2003/023457, "International Search Report of the International Searching Authority", Nov. 10, 2003, 3 pages.

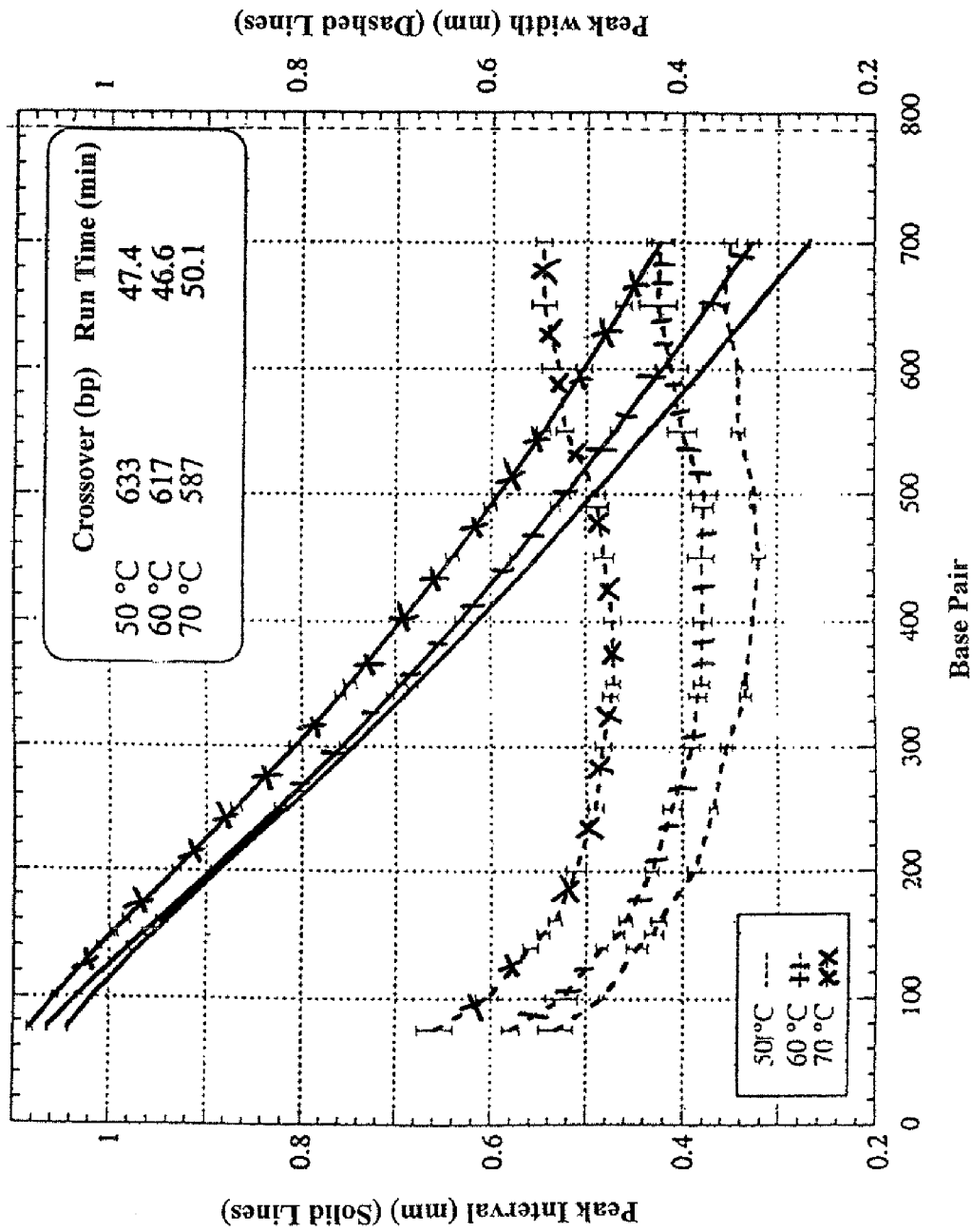
Figure 1: Performance of IC3 in CE DNA sequencing

GRAFT COPOLYMERS, THEIR PREPARATION AND USE IN CAPILLARY ELECTROPHORESIS

This application is a Continuation application of U.S. patent application Ser. No. 10/629,524, filed on Jul. 29, 2003 now abandoned, and claims the benefit of U.S. provisional application No. 60/399,662 filed Jul. 29, 2002, and U.S. provisional application No. 60/399,663 filed Jul. 29, 2002, the disclosure of each provisional application being incorporated by reference herein in its entirety.

1. FIELD OF THE INVENTION

The invention relates generally to graft copolymers, their preparation, and electrophoresis separation compositions comprising the same; also to ultra-high molecular weight poly(N,N-dimethylacrylamide) polymers, their preparation, and electrophoresis separation compositions comprising the same; and more particularly to supports, such as capillaries, containing these polymers and methods for separating biomolecules, especially polynucleotides, using capillary electrophoresis.

2. BACKGROUND OF THE INVENTION

The technique of capillary electrophoresis ("CE") is a widely used analytical method because of several technical advantages that it provides, namely: (i) capillaries containing a separation medium have high surface-to-volume ratios and dissipate heat efficiently which, in turn, permits high voltage fields to be used for rapid separations; (ii) minimal sample volume is needed; (iii) superior resolution is attainable; and (iv) the technique can easily be automated, e.g., Camilleri, Ed., *Capillary Electrophoresis: Theory and Practice* (CRC Press, Boca Raton, 1993); Grossman et al., Eds., *Capillary Electrophoresis* (Academic Press, San Diego, 1992). Because of these advantages, there has been great interest in applying CE to the separation of biomolecules, particularly in nucleic acid analysis. The need for rapid and accurate separation of nucleic acids, particularly deoxyribonucleic acid ("DNA") arises in the analysis of polymerase chain reaction products and DNA sequencing fragment analysis, e.g., Williams, *Methods* 4:227-232 (1992); Drossman et al., *Anal. Chem.*, 62:900-903 (1990); Huang et al., *Anal. Chem.*, 64:2149-2154 (1992); Swerdlow et al., *Nucleic Acids Research*, 18:1415-1419 (1990).

The citation of any reference in Section 2 of this application is not an admission that the reference is prior art to the application.

3. SUMMARY OF THE INVENTION

A first embodiment of the invention relates to poly($M_1$-g-$M_2$) or a salt thereof, where:

(a) each $M_1$ has the formula (I):

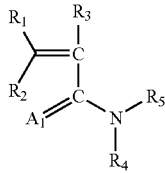

where each $A_1$ is independently O, S or $NX_1$;

each of $R_1$, $R_2$, $R_3$ and $R_4$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl) or —($C_5$-$C_{12}$ aryl)($C_1$-$C_{20}$ alkyl);

each $R_5$ is independently $C_1$-$C_{20}$ alkyl, $C_1$-$C_{20}$ heteroalkyl, $C_4$-$C_{12}$ cycloalkyl, $C_4$-$C_{12}$ heterocycloalkyl, $C_5$-$C_{12}$ aryl, $C_4$-$C_{12}$ heteroaryl, —($C_1$-$C_{20}$ alkyl)($C_4$-$C_{12}$ cycloalkyl), —($C_4$-$C_{12}$ cycloalkyl)($C_1$-$C_{20}$ alkyl), —($C_1$-$C_{20}$ heteroalkyl)($C_4$-$C_{12}$ cycloalkyl), —($C_4$-$C_{12}$ cycloalkyl)($C_1$-$C_{20}$ heteroalkyl), —($C_1$-$C_{20}$ alkyl)($C_4$-$C_{12}$ heterocycloalkyl), —($C_4$-$C_{12}$ heterocycloalkyl)($C_1$-$C_{20}$ alkyl), —($C_1$-$C_{20}$ heteroalkyl)($C_4$-$C_{12}$ heterocycloalkyl), —($C_4$-$C_{12}$ heterocycloalkyl)($C_1$-$C_{20}$ heteroalkyl), —($C_1$-$C_{20}$ alkyl)($C_5$-$C_{12}$ aryl), —($C_5$-$C_{12}$ aryl)($C_1$-$C_{20}$ alkyl), —($C_1$-$C_{20}$ heteroalkyl)($C_5$-$C_{12}$ aryl), —($C_5$-$C_{12}$ aryl)($C_1$-$C_{20}$ heteroalkyl), —($C_1$-$C_{20}$ alkyl)($C_4$-$C_{12}$ heteroaryl), —($C_4$-$C_{12}$ heteroaryl)($C_1$-$C_{20}$ alkyl), —($C_1$-$C_{20}$ heteroalkyl)($C_4$-$C_{12}$ heteroaryl), —($C_4$-$C_{12}$ heteroaryl)($C_1$-$C_{20}$ heteroalkyl), —($C_1$-$C_4$ alkyl)$_q$$NH_2$, —($C_1$-$C_4$ alkyl)$_q$$CONH_2$, —($C_1$-$C_4$ alkyl)$NHCONH_2$, —($C_1$-$C_4$ alkyl)$NHCOH$ or —($C_1$-$C_4$ alkyl)$_q$$NHCOCH_3$, where each q is 0 or 1; and each $X_1$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl), —($C_5$-$C_{12}$ aryl)($C_1$-$C_{20}$ alkyl), —($C_1$-$C_4$ alkyl)$_q$$NH_2$, —($C_1$-$C_4$ alkyl)$_q$$CONH_2$, —($C_1$-$C_4$ alkyl)$NHCONH_2$, —($C_1$-$C_4$ alkyl)$_q$$NHCOH$ or —($C_1$-$C_4$ alkyl)$_q$$NHCOCH_3$, where each q is 0 or 1;

(b) each $M_2$ has the formula (II):

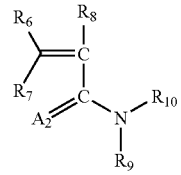

where each $A_2$ is independently O, S or $NX_2$;

each of $R_6$, $R_7$, $R_8$ and $R_9$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl) or —($C_5$-$C_{12}$ aryl)($C_1$-$C_{20}$ alkyl);

each $R_{10}$ is independently H, $C_1$-$C_{20}$ alkyl, $C_1$-$C_{20}$ heteroalkyl, $C_4$-$C_{12}$ cycloalkyl, $C_4$-$C_{12}$ heterocycloalkyl, $C_5$-$C_{12}$ aryl, $C_4$-$C_{12}$ heteroaryl, —($C_1$-$C_{20}$ alkyl)($C_4$-$C_{12}$ cycloalkyl), —($C_4$-$C_{12}$ cycloalkyl)($C_1$-$C_{20}$ alkyl), —($C_1$-$C_{20}$ heteroalkyl)($C_4$-$C_{12}$ cycloalkyl), —($C_4$-$C_{12}$ cycloalkyl)($C_1$-$C_{20}$ heteroalkyl), —($C_1$-$C_{20}$ alkyl)($C_4$-$C_{12}$ heterocycloalkyl), —($C_4$-$C_{12}$ heterocycloalkyl)($C_1$-$C_{20}$ alkyl), —($C_1$-$C_{20}$ heteroalkyl)($C_4$-$C_{12}$ heterocycloalkyl), —($C_4$-$C_{12}$ heterocycloalkyl)($C_1$-$C_{20}$ heteroalkyl), —($C_1$-$C_{20}$ alkyl)($C_5$-$C_{12}$ aryl), —($C_5$-$C_{12}$ aryl)($C_1$-$C_{20}$ alkyl), —($C_1$-$C_{20}$ heteroalkyl)($C_5$-$C_{12}$ aryl), —($C_5$-$C_{12}$ aryl)($C_1$-$C_{20}$ heteroalkyl), —($C_1$-$C_{20}$ alkyl)($C_4$-$C_{12}$ heteroaryl), —($C_4$-$C_{12}$ heteroaryl)($C_1$-$C_{20}$ alkyl), —($C_1$-$C_{20}$ heteroalkyl)($C_4$-$C_{12}$ heteroaryl), —($C_4$-$C_{12}$ heteroaryl)($C_1$-$C_{20}$ heteroalkyl), —($C_1$-$C_4$ alkyl)$_q$$NH_2$, —($C_1$-$C_4$ alkyl)$_q$$CONH_2$, —($C_1$-$C_4$ alkyl)$NHCONH_2$, —($C_1$-$C_4$ alkyl)$NHCOH$ or —($C_1$-$C_4$ alkyl)$_q$$NHCOCH_3$, where each q is 0 or 1; and each $X_2$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl), —($C_5$-$C_{12}$ aryl)($C_1$-$C_{20}$ alkyl), —($C_1$-$C_4$ alkyl)$_q$$NH_2$, —($C_1$-$C_4$ alkyl)$_q$$CONH_2$, —($C_1$-

$C_4$ alkyl)$NHCONH_2$, $—(C_1-C_4$ alkyl)$_q NHCOH$ or $—(C_1-C_4$ alkyl)$_q NHCOCH_3$, where each q is 0 or 1;

(c) provided that at least one $M_1$ is different from at least one $M_2$ and that at least one $A_1$ or $A_2$ is not O.

A second embodiment of the invention relates to ultra-high molecular weight poly(N,N-dimethylacrylamide) where the weight-average molecular weight of the poly(N,N-dimethylacrylamide) is at least about 3 MDaltons.

A third embodiment of the invention relates to a method for making ultra-high molecular weight poly(N,N-dimethylacrylamide), comprising the step of polymerizing N,N-dimethylacrylamide in an inverse emulsion comprising an oil phase, an aqueous phase, a surfactant and an initiator, to provide poly(N,N-dimethylacrylamide) with a weight-average molecular weight of at least about 3 MDaltons.

A fourth embodiment of the invention relates to a method for making poly($M_1$-g-$M_2$) comprising the step of polymerizing $M_2$ in the presence of an $M_1$ backbone polymer, i.e., "poly($M_1$)," to provide poly($M_1$-g-$M_2$).

A fifth embodiment of the invention relates to a composition comprising poly($M_1$-g-$M_2$) or a salt thereof and a buffer.

A sixth embodiment of the invention relates to a composition comprising ultra-high molecular weight poly(N,N-dimethylacrylamide) and a buffer.

A seventh embodiment of the invention relates to a method for making a composition of the invention, comprising contacting poly($M_1$-g-$M_2$) or a salt thereof with a buffer.

An eighth embodiment of the invention relates to a method for making a composition of the invention, comprising contacting ultra-high molecular weight poly(N,N-dimethylacrylamide) with a buffer.

A ninth embodiment of the invention relates to a method for separating a mixture of biomolecules, comprising:
(a) contacting a composition of the invention with a mixture comprising a biomolecule; and
(b) applying an electric field to the composition in an amount sufficient to facilitate the separation of a biomolecule from the mixture.

A tenth embodiment of the invention relates to a capillary containing a composition of the invention.

These and other objects, features and advantages of the present invention will become better understood with reference to the following description and drawing.

4. BRIEF DESCRIPTION OF THE DRAWINGS

FIG. 1 shows the CE performance of composition IC3 in DNA sequencing.

5. DETAILED DESCRIPTION OF THE INVENTION

The invention relates generally to graft copolymers, their preparation, and compositions comprising the same; also to ultra-high molecular weight poly(N,N-dimethylacrylamide) polymers, their preparation, and compositions comprising the same; and more particularly to supports, such as capillaries, containing these polymers and methods for separating biomolecules, especially polynucleotides, using capillary electrophoresis. The graft copolymers are surprisingly and unexpectedly effective in, e.g., electrophoresis separation media and for use in CE as dynamic coating polymers that effectively suppress electroosmosis or electroosmotic flow ("EOF"), which refers to capillary fluid flow induced by an electrical field. An exemplary graft copolymer of the invention can be described as a poly(DMA) ("PDMA") backbone polymer bearing polyacrylamide ("PAAm") side-chains or pendant chains.

As used herein, a "copolymer" includes a polymer comprising at least two different monomeric subunits. Thus, a polymeric chain made up of three different monomers (also known as a terpolymer) is included within the term "copolymer," as are polymer chains containing more than three different monomeric units. Copolymers may be formed in many ways known to those of ordinary skill in the art, for example: by polymerizing two different monomers; by block copolymerization; by graft copolymerization, e.g., where an existing polymer chain is further reacted with a different monomer; and by a post-polymerization reaction, e.g., where a polymer with ester side groups is partially hydrolyzed. As used herein, the term "polymer" includes a homopolymer and a copolymer.

It is conventional in the polymer art that graft copolymers are commonly named as "poly($M_1$-g-$M_2$)," where $M_1$ refers to the monomer or monomers making up the backbone polymer or backbone copolymer, i.e., poly($M_1$); and $M_2$ (following the "g" for graft) refers to the monomer or monomers making up the grafted polymer or grafted copolymer, i.e., "poly($M_2$)," sometimes also referred to herein as the pendant, pendant polymer, pendant chain or side-chain polymer. It is to be understood that poly($M_1$) and poly($M_2$) can be the same or different homopolymer or copolymer. See G. Odian, *Principles of Polymerization*, McGraw-Hill Book Co., New York, 1970, pp. 366, 633 and U.S. Pat. No. 6,319,976 B1 to DeNicola, Jr. et al. for a further explanation and examples of this nomenclature.

For example, poly(N,N-dimethylacrylamide-g-acrylamide) denotes a graft copolymer where the backbone polymer is poly(N,N-dimethylacrylamide) and the pendant polymer is poly(acrylamide), poly((N,N-dimethylacrylamide-co-N,N-diethyl-methacrylamide)-g-acrylamide) denotes a graft copolymer where the backbone polymer is a copolymer of N,N-dimethylacrylamide and N,N-diethyl-methacrylamide and the pendant polymer is poly(acrylamide), and poly(N,N-dimethylacrylamide-g-(acrylamide-co-N-butoxymethyl-methacrylamide-co-N-methoxymethyl-acrylamide) denotes a graft copolymer where the backbone polymer is poly(N,N-dimethylacrylamide) and the pendant polymer is a copolymer of acrylamide, N-butoxymethyl-methacrylamide and N-methoxymethyl-acrylamide.

5.1 Graft Copolymer Poly($M_1$-g-$M_2$)

The first embodiment of the invention relates to graft copolymer poly($M_1$-g-$M_2$) or a salt thereof, where:
(a) each $M_1$ has the formula (I):

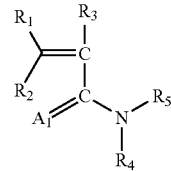

where each $A_1$ is independently O, S or $NX_1$;
each of $R_1, R_2, R_3$ and $R_4$ is independently H, $C_1-C_{20}$ alkyl, $C_4-C_{12}$ cycloalkyl, $C_5-C_{12}$ aryl, $C_4-C_{12}$ heteroaryl, —($C_1-C_{20}$ alkyl)($C_5-C_{12}$ aryl) or —($C_5-C_{12}$ aryl)($C_1-C_{20}$ alkyl);
each $R_5$ is independently $C_1-C_{20}$ alkyl, $C_1-C_{20}$ heteroalkyl, $C_4-C_{12}$ cycloalkyl, $C_4-C_{12}$ heterocycloalkyl, $C_5-C_{12}$ aryl, $C_4-C_{12}$ heteroaryl, —($C_1-C_{20}$ alkyl)($C_4-C_{12}$ cycloalkyl), —($C_4$-$C_{12}$ cycloalkyl)($C_1$-$C_{20}$ alkyl), —($C_1$-$C_{20}$ heteroalkyl)($C_4$-$C_{12}$ cycloalkyl), —($C_4$-$C_{12}$ cycloalkyl)($C_1$-$C_{20}$ heteroalkyl), —($C_1$-$C_{20}$ alkyl)($C_4$-$C_{12}$ heterocycloalkyl), —($C_4$-$C_{12}$ heterocycloalkyl)($C_1$-$C_{20}$ alkyl), —($C_1$-$C_{20}$ heteroalkyl)($C_4$-$C_{12}$ heterocycloalkyl), —($C_4$-$C_{12}$ heterocycloalkyl)($C_1$-$C_{20}$ heteroalkyl), —($C_1$-$C_{20}$ alkyl)($C_5$-$C_{12}$ aryl), —($C_5$-$C_{12}$ aryl)($C_1$-$C_{20}$ alkyl), —($C_1$-$C_{20}$ heteroalkyl)($C_5$-$C_{12}$ aryl), —($C_5$-$C_{12}$ aryl)($C_1$-$C_{20}$ heteroalkyl), —($C_1$-$C_{20}$ alkyl)($C_4$-$C_{12}$ heteroaryl), —($C_4$-$C_{12}$ heteroaryl)($C_1$-$C_{20}$ alkyl), —($C_1$-$C_{20}$ heteroalkyl)($C_4$-$C_{12}$ heteroaryl), —($C_4$-$C_{12}$ heteroaryl)($C_1$-$C_{20}$ heteroalkyl), —($C_1$-$C_4$ alkyl)$_q$$NH_2$, —($C_1$-$C_4$ alkyl)$_q$$CONH_2$, —($C_1$-$C_4$ alkyl)NHCONH$_2$, —($C_1$-$C_4$ alkyl)NHCOH or —($C_1$-$C_4$ alkyl)$_q$NHCOCH$_3$, where each q is 0 or 1; and each $X_1$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl), —($C_5$-$C_{12}$ aryl)($C_1$-$C_{20}$ alkyl), —($C_1$-$C_4$ alkyl)$_q$$NH_2$, —($C_1$-$C_4$ alkyl)$_q$$CONH_2$, —($C_1$-$C_4$ alkyl)NHCONH$_2$, —($C_1$-$C_4$ alkyl)$_q$NHCOH or —($C_1$-$C_4$ alkyl)$_q$NHCOCH$_3$, where each q is 0 or 1;

(b) each $M_2$ has the formula (II):

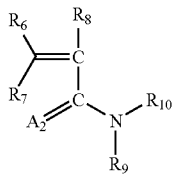

where each $A_2$ is independently O, S or NX$_2$;

each of $R_6$, $R_7$, $R_8$ and $R_9$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl) or —($C_5$-$C_{12}$ aryl)($C_1$-$C_{20}$ alkyl);

each $R_{10}$ is independently H, $C_1$-$C_{20}$ alkyl, $C_1$-$C_{20}$ heteroalkyl, $C_4$-$C_{12}$ cycloalkyl, $C_4$-$C_{12}$ heterocycloalkyl, $C_5$-$C_{12}$ aryl, $C_4$-$C_{12}$ heteroaryl, —($C_1$-$C_{20}$ alkyl)($C_4$-$C_{12}$ cycloalkyl), —($C_4$-$C_{12}$ cycloalkyl)($C_1$-$C_{20}$ alkyl), —($C_1$-$C_{20}$ heteroalkyl)($C_4$-$C_{12}$ cycloalkyl), —($C_4$-$C_{12}$ cycloalkyl)($C_1$-$C_{20}$ heteroalkyl), —($C_1$-$C_{20}$ alkyl)($C_4$-$C_{12}$ heterocycloalkyl), —($C_4$-$C_{12}$ heterocycloalkyl)($C_1$-$C_{20}$ alkyl), —($C_1$-$C_{20}$ heteroalkyl)($C_4$-$C_{12}$ heterocycloalkyl), —($C_4$-$C_{12}$ heterocycloalkyl)($C_1$-$C_{20}$ heteroalkyl), —($C_1$-$C_{20}$ alkyl)($C_5$-$C_{12}$ aryl), —($C_5$-$C_{12}$ aryl)($C_1$-$C_{20}$ alkyl), —($C_1$-$C_{20}$ heteroalkyl)($C_5$-$C_{12}$ aryl), —($C_5$-$C_{12}$ aryl)($C_1$-$C_{20}$ heteroalkyl), —($C_1$-$C_{20}$ alkyl)($C_4$-$C_{12}$ heteroaryl), —($C_4$-$C_{12}$ heteroaryl)($C_1$-$C_{20}$ alkyl), —($C_1$-$C_{20}$ heteroalkyl)($C_4$-$C_{12}$ heteroaryl), —($C_4$-$C_{12}$ heteroaryl)($C_1$-$C_{20}$ heteroalkyl), —($C_1$-$C_4$ alkyl)$_q$$NH_2$, —($C_1$-$C_4$ alkyl)$_q$$CONH_2$, —($C_1$-$C_4$ alkyl)NHCONH$_2$, —($C_1$-$C_4$ alkyl)NHCOH or —($C_1$-$C_4$ alkyl)$_q$NHCOCH$_3$, where each q is 0 or 1; and each $X_2$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl), —($C_5$-$C_{12}$ aryl)($C_1$-$C_{20}$ alkyl), —($C_1$-$C_4$ alkyl)$_q$$NH_2$, —($C_1$-$C_4$ alkyl)$_q$$CONH_2$, —($C_1$-$C_4$ alkyl)NHCONH$_2$, —($C_1$-$C_4$ alkyl)$_q$NHCOH or —($C_1$-$C_4$ alkyl)$_q$NHCOCH$_3$, where each q is 0 or 1;

(c) provided that at least one $M_1$ is different from at least one $M_2$ and that at least one $A_1$ or $A_2$ is not O.

It is to be understood that each $M_1$ or each $M_2$ of poly($M_1$-g-$M_2$) or a salt thereof need not be identical. Rather poly($M_1$-g-$M_2$) or a salt thereof can comprise non-identical $M_1$ and $M_2$ groups, i.e., the backbone, the pendant or both can be copolymers. In other embodiments, however, each $M_1$ or each $M_2$ is identical. In certain embodiments, each $M_1$ and each $M_2$ is identical.

In certain embodiments, for each $M_1$, $R_1$ and $R_2$ are H, and $R_3$ is H or methyl; and for each $M_2$, $R_6$ and $R_7$ are H, and $R_8$ is H or methyl.

As used herein, the term "alkyl" refers to a straight or branched hydrocarbon chain. Examples of alkyl groups include lower alkyl, for example, methyl, ethyl, n-propyl, iso-propyl, n-butyl, iso-butyl, tert-butyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, pentyl, isopentyl, neopentyl, hexyl and the like; upper alkyl, for example, n-heptyl, n-octyl, iso-octyl, ethylhexyl, nonyl, decyl, dodecyl, octadecyl and the like. The ordinary skilled artisan is familiar with numerous straight, i.e., linear, and branched alkyl groups, which are within the scope of the present invention. In addition, such alkyl groups may also include heteroalkyl groups.

The term "heteroalkyl" in the context of the present invention broadly refers to an alkyl possessing in-chain, pendant and/or terminal functionality, as understood by those persons of ordinary skill in the relevant art. As examples of in-chain functionality may be mentioned a carbonyl group or groups (which is/are, of course, included in the carbon count), heteroatom or heteroatoms (such as at least one oxygen, sulfur, nitrogen, phosphorous or silicon) in the chain, esters, amides, urethanes and their thio-derivatives, i.e., where at least one oxygen atom is replaced by a sulfur atom. As examples of pendant and/or terminal functionality may be mentioned hydrogen-containing groups such as hydroxyl, amino, aldehyde, carboxyl, thio and amido, and halogen. Thus, exemplary heteroalkyl groups include butoxymethyl, dimethoxybutyl, dimethoxyethyl, 3-(trimethylammonium chloride)-propyl, trimethylbutyl, acetyl, glycolic acid methyl ester, hydroxymethyl, methoxymethyl, methoxypropyl, 2,2,2-trichloro-1-hydroxyethyl, tri(hydroxymethyl)-methyl, pentafluoroethyl, bromo, chloro, 3-iodopropyl and the like.

As used herein, the term "cycloalkyl" refers to a monocyclic or polycyclic ring comprising carbon and hydrogen atoms and having no carbon-carbon multiple bonds. Examples of cycloalkyl groups include $C_3$-$C_7$ cycloalkyl groups, such as cyclopropyl, cyclobutyl, cyclopentyl, cyclohexyl and cycloheptyl, adamantyl, saturated cyclic and bicyclic terpenes and the like. A cycloalkyl group can be unsubstituted or substituted by one or more suitable substituents.

As used herein, the term "heterocycloalkyl" refers to a cycloalkyl group comprising a heteroatom (such as at least one oxygen, sulfur, nitrogen, phosphorous, halogen or silicon), e.g., in the ring and/or pendant thereto. Thus, a heterocycloalkyl group can be unsubstituted or substituted with one or more substituents. Examples of heterocycloalkyl groups include pyrrolidinyl, pyrrolidino, piperidinyl, piperidino, piperazinyl, piperazino, morpholinyl, morpholino, thiomorpholinyl, thiomorpholino and the like.

As used herein, the term "aryl" refers to a monocyclic or polycyclic-aromatic radical comprising a hydrocarbon ring(s) bearing a system of conjugated double bonds. In certain embodiments, the polycyclic-aromatic radical comprising a hydrocarbon ring(s) bearing a system of conjugated double bonds comprises at least six π (pi) electrons. An aryl group can be unsubstituted or substituted with one or more substituents. Examples of aryl groups include phenyl, anthacenyl, fluorenyl, indenyl, azulenyl, naphthyl, anisyl, toluoyl, xylenyl and the like.

As used herein, the term "heteroaryl" refers to an aryl group comprising a heteroatom (such as at least one oxygen, sulfur, nitrogen, phosphorous, halogen or silicon), e.g., in the ring and/or pendant thereto. Thus, a heteroaryl group can be unsubstituted or substituted with one or more substituents. Examples of heteroaryl groups include halophenyl, nitrophenyl, hydroxyphenyl, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, thiazolyl, furyl, phienyl, isoxazolyl, oxazolyl, isoquinolinyl, dihydroxyisoquinolinyl, isoquinolinonyl, quinazolinyl, quinazolinonyl, naphthalimidyl, phenanthridinonyl and the like.

As used herein, a "compound term," e.g., -(cycloalkyl) (alkyl), broadly refers to a monovalent first group, here cycloalkyl, in which the valency is derived by abstraction of a hydrogen from a carbon atom or suitable heteroatom, where the first group is further substituted by at least one second group, here an alkyl group(s), e.g., 3-methylcyclohexyl or isobornyl. As a further illustration, a compound term such as -(alkyl)(aryl) refers to a first group, here alkyl, which is further substituted with at least one second group, here an aryl group(s), e.g., benzyl or 2,2-diphenyl ethyl.

As used herein, a "salt" of a polymer refers to a polymer having at least one anionic charge, cationic charge, or both, e.g., an amphoteric polymer, where each charge has associated with it a suitable counterion. "Counterion" refers to an ion that balances the polymer's anionic or cationic charge. Exemplary counterions for a polymer comprising a cationic charge include chloride, bromide, iodide, hydroxide, alkoxide, carbonate, bicarbonate, oxide, formate, sulfate, benzene sulfonate, p-toluenesulfonate, p-bromobenzenesulfonate, methanesulfonate, trifluoromethanesulfonate, phosphate, perchlorate, tetrafluoroborate, tetraphenylboride, nitrate and anions of aromatic or aliphatic carboxylic acids. Exemplary counterions for a polymer comprising an anionic charge include ammonium, quaternary phosphonium, such as a tetraalkyl phosphonium halide, and the cations of Li, Na, K, Rb, Cs and Ag. In certain embodiments, the counterions include chloride, p-toluenesulfonate, lithium, sodium and potassium.

In an embodiment of the invention, the graft copolymer is poly($M_1$-g-$M_2$) or a salt thereof, where:
(a) $M_1$ is N-adamantyl-acrylamide, N-butoxymethyl-acrylamide, N,N-dibutyl-acrylamide, N,N-diethyl-acrylamide, N-4,4-dimethoxybutyl-acrylamide, N,N-dimethyl-acrylamide, N,N-dipropyl-acrylamide, N-dodecyl-acrylamide, N-2-ethylhexyl-acrylamide, N-isobornyl-acrylamide, N-methyl-, N-2,2-dimethoxyethyl-acrylamide, N-morpholinoethyl-acrylamide, N-octadecyl-acrylamide, N-3-(trimethylammonium)-propyl-acrylamide chloride, N-1,1,3-trimethylbutyl-acrylamide, N-adamantyl-methacrylamide, N-butoxymethyl-methacrylamide, N,N-dibutyl-methacrylamide, N,N-diethyl-methacrylamide, N-4,4-dimethoxybutyl-methacrylamide, N,N-dimethyl-methacrylamide, N,N-dipropyl-methacrylamide, N-dodecyl-methacrylamide, N-2-ethylhexyl-methacrylamide, N-isobornyl-methacrylamide, N-methyl-, N-2,2-dimethoxyethyl-methacrylamide, N-morpholinoethyl-methacrylamide, N-octadecyl-methacrylamide, N-3-(trimethylammonium)-propyl-methacrylamide chloride, N-1,1,3-trimethylbutyl-methacrylamide, or a mixture thereof;
(b) $M_2$ is acrylamide, N-acetyl-acrylamide, N-butoxymethyl-acrylamide, N-4,4-dimethoxybutyl-acrylamide, N-2,2-dimethoxyethyl-acrylamide, N-2-glycolic acid methyl ester acrylamide, N-hydroxymethyl-acrylamide, N-methoxymethyl-acrylamide, N-3-methoxypropyl-acrylamide, N-methyl-, N-2,2-dimethoxyethyl-acrylamide, N-morpholinoethyl-acrylamide, N-2,2,2-trichloro-1-hydroxyethyl-acrylamide, N-tri(hydroxymethyl)-methyl-acrylamide, methacrylamide, N-acetyl-methacrylamide, N-butoxymethyl-methacrylamide, N-4,4-dimethoxybutyl-methacrylamide, N-2,2-dimethoxyethyl-methacrylamide, N-2-glycolic acid methyl ester methacrylamide, N-hydroxymethyl-methacrylamide, N-methoxymethyl-methacrylamide, N-3-methoxypropyl-methacrylamide, N-methyl-, N-2,2-dimethoxyethyl-methacrylamide, N-morpholinoethyl-methacrylamide, N-2,2,2-trichloro-1-hydroxyethyl-methacrylamide, N-tri(hydroxymethyl)-methyl-methacrylamide, or a mixture thereof;
(c) provided that at least one $M_1$ is different from at least one $M_2$.

In another embodiment of the invention, the graft copolymer is poly($M_1$-g-$M_2$) or a salt thereof, where:
(a) $M_1$ is N-adamantyl-acrylamide, N-butoxymethyl-acrylamide, N,N-dibutyl-acrylamide, N,N-diethyl-acrylamide, N-4,4-dimethoxybutyl-acrylamide, N,N-dimethyl-acrylamide, N,N-dipropyl-acrylamide, N-dodecyl-acrylamide, N-2-ethylhexyl-acrylamide, N-isobornyl-acrylamide, N-methyl-, N-2,2-dimethoxyethyl-acrylamide, N-morpholinoethyl-acrylamide, N-octadecyl-acrylamide, N-3-(trimethylammonium)-propyl-acrylamide chloride, N-1,1,3-trimethylbutyl-acrylamide, N-adamantyl-methacrylamide, N-butoxymethyl-methacrylamide, N,N-dibutyl-methacrylamide, N,N-diethyl-methacrylamide, N-4,4-dimethoxybutyl-methacrylamide, N,N-dimethyl-methacrylamide, N,N-dipropyl-methacrylamide, N-dodecyl-methacrylamide, N-2-ethylhexyl-methacrylamide, N-isobornyl-methacrylamide, N-methyl-, N-2,2-dimethoxyethyl-methacrylamide, N-morpholinoethyl-methacrylamide, N-octadecyl-methacrylamide, N-3-(trimethylammonium)-propyl-methacrylamide chloride, N-1,1,3-trimethylbutyl-methacrylamide, or a mixture thereof;
(b) $M_2$ is N-acetyl-acrylamide, N-butoxymethyl-acrylamide, N-4,4-dimethoxybutyl-acrylamide, N-2,2-dimethoxyethyl-acrylamide, N-2-glycolic acid methyl ester acrylamide, N-hydroxymethyl-acrylamide, N-methoxymethyl-acrylamide, N-3-methoxypropyl-acrylamide, N-methyl-, N-2,2-dimethoxyethyl-acrylamide, N-morpholinoethyl-acrylamide, N-2,2,2-trichloro-1-hydroxyethyl-acrylamide, N-tri(hydroxymethyl)-methyl-acrylamide, methacrylamide, N-acetyl-methacrylamide, N-butoxymethyl-methacrylamide, N-4,4-dimethoxybutyl-methacrylamide, N-2,2-dimethoxyethyl-methacrylamide, N-2-glycolic acid methyl ester methacrylamide, N-hydroxymethyl-methacrylamide, N-methoxymethyl-methacrylamide, N-3-methoxypropyl-methacrylamide, N-methyl-, N-2,2-dimethoxyethyl-methacrylamide, N-morpholinoethyl-methacrylamide, N-2,2,2-trichloro-1-hydroxyethyl-methacrylamide, N-tri(hydroxymethyl)-methyl-methacrylamide, or a mixture thereof;
(c) provided that at least one $M_1$ is different from at least one $M_2$.

In another embodiment of the invention, the graft copolymer is poly($M_1$-g-$M_2$) or a salt thereof, where:
(a) $M_1$ is N-adamantyl-acrylamide, N-butoxymethyl-acrylamide, N,N-dibutyl-acrylamide, N,N-diethyl-acrylamide, N-4,4-dimethoxybutyl-acrylamide, N,N-dimethyl-acrylamide, N,N-dipropyl-acrylamide, N-dodecyl-acrylamide, N-2-ethylhexyl-acrylamide, N-isobornyl-acrylamide, N-methyl-, N-2,2-dimethoxyethyl-acrylamide, N-morpholinoethyl-acrylamide, N-octadecyl-acrylamide, N-3-(trimethylammonium)-propyl-acrylamide chloride, N-1,1,3-trimethylbutyl-acrylamide, N-adamantyl-methacrylamide, N-butoxymethyl-methacrylamide, N,N-dibutyl-methacrylamide, N,N-diethyl-methacrylamide, N-4,4-dimethoxybutyl-methacrylamide, N,N-dimethyl-methacrylamide, N,N-dipropyl-methacrylamide, N-dodecyl-methacrylamide, N-2-ethylhexyl-methacrylamide, N-isobornyl-methacrylamide, N-methyl-, N-2,2-dimethoxyethyl-methacrylamide, N-morpholinoethyl-methacrylamide, N-octadecyl-methacrylamide, N-3-(trimethylammonium)-propyl-methacrylamide chloride, N-1,1,3-trimethylbutyl-methacrylamide, or a mixture thereof;

(b) $M_2$ is N-acetyl-acrylamide, N-butoxymethyl-acrylamide, N-4,4-dimethoxybutyl-acrylamide, N-2,2-dimethoxyethyl-acrylamide, N-2-glycolic acid methyl ester acrylamide, N-hydroxymethyl-acrylamide, N-methoxymethyl-acrylamide, N-3-methoxypropyl-acrylamide, N-methyl-, N-2,2-dimethoxyethyl-acrylamide, N-morpholinoethyl-acrylamide, N-2,2,2-trichloro-1-hydroxyethyl-acrylamide, N-tri(hydroxymethyl)-methyl-acrylamide, N-acetyl-methacrylamide, N-butoxymethyl-methacrylamide, N-4,4-dimethoxybutyl-methacrylamide, N-2,2-dimethoxyethyl-methacrylamide, N-2-glycolic acid methyl ester methacrylamide, N-hydroxymethyl-methacrylamide, N-methoxymethyl-methacrylamide, N-3-methoxypropyl-methacrylamide, N-methyl-, N-2,2-dimethoxyethyl-methacrylamide, N-morpholinoethyl-methacrylamide, N-2,2,2-trichloro-1-hydroxyethyl-methacrylamide, N-tri(hydroxymethyl)-methyl-methacrylamide, or a mixture thereof;

(c) provided that at least one $M_1$ is different from at least one $M_2$.

Alternately or in addition to $M_2$, the pendant can comprise poly(hydroxymethylene), poly(oxyethylene), poly(oxypropylene), poly(oxyethylene-co-oxypropylene), poly(vinyl alcohol), poly(vinylpyrrolidone), poly(2-ethyl-2-oxazoline), poly(2-methyl-2-oxazoline), poly((2-ethyl-2-oxazoline)-co-(2-methyl-2-oxazoline)), poly(N-acetamidoacrylamide), poly(acryloxylurea), water-soluble polysaccharides such as hydroxyethyl cellulose and hydroxymethyl cellulose, or a mixture thereof.

In another embodiment, the poly($M_1$-g-$M_2$) or a salt thereof is poly(N-butoxymethyl-acrylamide-g-acrylamide), poly(N,N-dibutyl-acrylamide-g-acrylamide), poly(N,N-diethyl-acrylamide-g-acrylamide), poly(N-4,4-dimethoxybutyl-acrylamide-g-acrylamide), poly(N,N-dimethyl-acrylamide-g-acrylamide), poly(N,N-dipropyl-acrylamide-g-acrylamide), poly(N-2-ethylhexyl-acrylamide-g-acrylamide), poly(N-isobornyl-acrylamide-g-acrylamide), poly(N-3-(trimethylammonium)-propyl-acrylamide chloride-g-acrylamide), poly(N-1,1,3-trimethylbutyl-acrylamide-g-acrylamide), poly(N-butoxymethyl-methacrylamide-g-acrylamide), poly(N,N-dibutyl-methacrylamide-g-acrylamide), poly(N,N-diethyl-methacrylamide-g-acrylamide), poly(N-4,4-dimethoxybutyl-methacrylamide-g-acrylamide), poly(N,N-dimethyl-methacrylamide-g-acrylamide), poly(N,N-dipropyl-methacrylamide-g-acrylamide), poly(N-1,1,3-trimethylbutyl-methacrylamide-g-acrylamide), poly((N,N-dimethyl-acrylamide-co-N,N-dibutyl-acrylamide)-g-acrylamide), poly((N,N-dimethyl-acrylamide-co-N,N-dibutyl-methacrylamide)-g-acrylamide), poly((N,N-dimethyl-methacrylamide-co-N,N-dibutyl-acrylamide)-g-acrylamide), poly((N,N-dimethyl-methacrylamide-co-N,N-dibutyl-methacrylamide)-g-acrylamide), poly(N-butoxymethyl-acrylamide-g-(acrylamide-co-N-hydroxymethyl-acrylamide)), poly(N-butoxymethyl-acrylamide-g-(acrylamide-co-N-hydroxymethyl-methacrylamide)), poly(N-butoxymethyl-acrylamide-g-methacrylamide), poly(N,N-dibutyl-acrylamide-g-methacrylamide), poly(N,N-diethyl-acrylamide-g-methacrylamide), poly(N-4,4-dimethoxybutyl-acrylamide-g-methacrylamide), poly(N,N-dimethyl-acrylamide-g-methacrylamide), poly(N,N-dipropyl-acrylamide-g-methacrylamide), poly(N-2-ethylhexyl-acrylamide-g-methacrylamide), poly(N-isobornyl-acrylamide-g-methacrylamide), poly(N-3-(trimethylammonium)-propyl-acrylamide chloride-g-methacrylamide), poly(N-1,1,3-trimethylbutyl-acrylamide-g-methacrylamide), poly(N-butoxymethyl-methacrylamide-g-methacrylamide), poly(N,N-dibutyl-methacrylamide-g-methacrylamide), poly(N,N-diethyl-methacrylamide-g-methacrylamide), poly(N-4,4-dimethoxybutyl-methacrylamide-g-methacrylamide), poly(N,N-dimethyl-methacrylamide-g-methacrylamide), poly(N,N-dipropyl-methacrylamide-g-methacrylamide), poly(N-1,1,3-trimethylbutyl-methacrylamide-g-methacrylamide), poly((N,N-dimethyl-acrylamide-co-N,N-dibutyl-acrylamide)-g-methacrylamide), poly((N,N-dimethyl-acrylamide-co-N,N-dibutyl-methacrylamide)-g-methacrylamide), poly((N,N-dimethyl-methacrylamide-co-N,N-dibutyl-acrylamide)-g-methacrylamide), poly((N,N-dimethyl-methacrylamide-co-N,N-dibutyl-methacrylamide)-g-methacrylamide), poly(N-butoxymethyl-acrylamide-g-(methacrylamide-co-N-hydroxymethyl-acrylamide)), or poly(N-butoxymethyl-acrylamide-g-(methacrylamide-co-N-hydroxymethyl-methacrylamide)).

In one embodiment, $M_1$ is N,N-dimethylacrylamide and $M_2$ is acrylamide.

In another embodiment, a graft copolymer of the invention is water soluble, water swellable or both, at atmospheric pressure, a concentration of from about 0.01 to about 1 wt. %, and from about 20° C. to about 70° C., e.g., at 25° C. For purposes of this invention, water swellable graft copolymers are generally either those that swell in water but appear not to be completely soluble because they have a very slow dissolution rate, e.g., graft copolymers that are substantially uncrosslinked but have an extremely high weight-average molecular weight; or those unable to dissolve completely in water because they have been crosslinked to a certain low degree, for example, by synthesizing the copolymer to comprise certain amounts of crosslinking or branching agents. In one embodiment, a graft copolymer of the invention is substantially uncrosslinked such that it is able to flow into or out of a capillary either with or without the assistance of pressure or vacuum. In another embodiment, a graft copolymer of the invention is substantially uncrosslinked by covalent chemical bonds.

The weight-average molecular weight ("Mw") of the backbone polymer can vary widely. In one embodiment, the backbone polymer Mw is from about 50,000 Daltons ("Da"). In another embodiment, the backbone polymer Mw is from about 75,000 Da, to about 15 MegaDaltons ("MDa"). In another embodiment, the Mw of the backbone polymer is from about 100,000 Da to about 10 MDa. In another embodiment, the Mw of the backbone polymer is from about 500,000 Da to about 8 MDa. In another embodiment, the Mw of the backbone polymer is from about 800,000 Da to about 5 MDa.

The ratio of the pendant/backbone by weight, i.e., the sum of the weight of all $M_2$ units present in poly($M_1$-g-$M_2$) divided by the sum of the weight of all $M_1$ units present, can vary widely. In one embodiment, the ratio of the pendant/backbone is from about 0.01 to about 500. In another embodiment, the ratio of the pendant/backbone is from about 0.05 to about 200. In another embodiment, the ratio of the pendant/backbone is from about 0.1 to about 20 by weight.

The Mw of the poly($M_1$-g-$M_2$) can vary widely. In one embodiment, the Mw of the poly($M_1$-g-$M_2$) is from about 150,000 Da to about 20 MDa. In another embodiment, the Mw of the poly($M_1$-g-$M_2$) is from about 500,000 Da to about 10 MDa. In another embodiment, the Mw of the poly($M_1$-g-$M_2$) is from about 1 MDa to about 6 MDa.

The conventional method of gel permeation chromatography ("GPC"), also known as size exclusion chromatography or SEC, is a reliable way for determining the molecular weight of polymers and copolymers. The fundamentals of applying a multi-angle laser light scattering detector to GPC instrumentation ("GPC-MALLS") for the absolute characterization of polymers, such as the determination of their number-average and weight-average molecular weights, are conventional, e.g., see Wyatt, *Analytica Chimica Acta* 272:1-40 (1993). For example, GPC-MALLS has been used to determine, inter alia, the Mw of several water-soluble polymers and copolymers with molecular weights of from below 50,000 Da to over 1 MDa. Nagy, *Proc. Int'l. GPC Symposium*, Orlando, Fla., June 1994 95-0315:71-95 (1994). Moreover, the accuracy of GPC and, in particular, GPC-MALLS, for molecular weight determinations is well-recognized in the art. For example, the GPC molecular weight results obtained for identical polymer samples using several different advanced on-line detection systems, including GPC-MALLS compare favorably. S. Yau, *Chemtracts—Macromolecular Chemistry* 1:1-36 (1990). Therefore, GPC-MALLS is a convenient way for determining the number-average and weight-average molecular weights of poly($M_1$), poly($M_2$) and poly($M_1$-g-$M_2$) polymers of the invention.

5.2 Method for Making Graft Copolymer

Many methods of making graft copolymers are known in the art and can be used to prepare the poly($M_1$-g-$M_2$) of the present invention. For example, several such methods are summarized in the following chapter: Costello et al., "Copolymers" in *Kirk-Othmer Encyc. of Chem. Technol.*, 4th Ed., John Wiley & Sons, New York, 1993, Vol. 7, pp. 349-381. These conventional methods include selecting a polymeric backbone with suitable reactive sites, selecting a monomer or monomers, e.g., $M_2$ of the invention, and then conducting a polymerization, e.g., initiated by free-radical, anionic or cationic means, of that monomer(s) to form a graft copolymer. Id., pp. 356-358. Such polymerizations can, of course, be conducted in bulk, solution, suspension, emulsion or microemulsion, and a wide variety of polymerization initiators can be used. Id., p. 356.

Many types of free-radical initiators are suitable, e.g., azo and diazo compounds, such as azo-bis-isobutyronitrile ("AIBN"), organic peroxides, hydroperoxides, persulfates and hydropersulfates, such as benzoyl peroxide, inorganic peroxides and persulfates, such as the peroxide-redox systems, carbon-carbon initiators, such as hexasubstituted ethanes, and photoinitiators; numerous examples are known in the art. See Sanchez et al., "Initiators (Free-Radical)" in *Kirk-Othmer Encyc. of Chem. Technol.*, 4th Ed., John Wiley & Sons, New York, 1995, Vol. 14, pp. 431-460. Suitable anionic initiators are known in the art and include aromatic radical anions, such as sodium naphthalene; alkyl lithium compounds, such as t-butyl lithium; fluorenyl carbanions; 1,1-diphenylmethylcarbanions; cumyl potassium; and those described by Quirk et al., "Initiators (Anionic)" in *Kirk-Othmer Encyc. of Chem. Technol.*, 4th Ed., John Wiley & Sons, New York, 1995, Vol. 14, pp. 461-476. Suitable cationic initiators are also known in the art and include protic acids, cation donor (initiator)/Friedel-Crafts acid (coinitiator) systems, stable cation salts, and those described by Faust, "Initiators (Cationic)" in *Kirk-Othmer Encyc. of Chem. Technol.*, 4th Ed., John Wiley & Sons, New York, 1995, Vol. 14, pp. 476-482. The free-radical, anionic or cationic initiator may undergo decomposition by any known means, e.g., thermally or photolytically, when this is required to initiate polymerization.

A suitable backbone polymer, such as poly(N,N-dimethylacrylamide) ("PDMA"), can be synthesized using techniques known in the art, e.g., as disclosed in Trossarelli et al., *J. Polymer Sci.*, 57:445-452 (1962) and in U.S. Pat. No. 5,916,426 to Madabhushi et al.

In particular, eight examples of the free-radical initiated synthesis of PDMA in dioxane via solution-polymerization are disclosed in Example 1 of the latter, at col. 10, line 40 to col. 11, line 12, which is hereby incorporated by reference. The following representative procedure is suitably useful for forming satisfactory PDMA. From 5 to 70% g DMA per cc dioxane and from 1.2 to 16.4 mg of the free-radical initiator AIBN/g DMA are mixed at about 25° C. in an Erlenmeyer flask and argon gas is bubbled through the solution for 10 minutes at room temperature. DMA polymerization is initiated by raising the temperature to about 55° C. Polymerization times of from about 10 to about 25 minutes are satisfactory, depending upon the concentration of monomer. After polymerization, each of the polymers formed may be purified, e.g., by three cycles of precipitation in hexane and dissolution in methylene chloride. Finally, the hexane precipitate may be dried overnight in a vacuum desiccator and then lyophilized. The Mw of the PDMA product obtained, which may be conveniently determined using GPC, should be in the range of from about 54,000 to about 99,000 Da.

Additionally, four examples of the free-radical initiated synthesis of PDMA in tert-butyl alcohol via solution-polymerization are disclosed in Example 2 of U.S. Pat. No. 5,916,426, at col. 11, lines 13-35, which is hereby incorporated by reference. The tert-butyl alcohol acts not only as a solvent but as a chain transfer agent that reduces the PDMA molecular weight. The following representative procedure is alternatively useful for forming satisfactory PDMA. From 50 to 70% g DMA per cc tert-butyl alcohol and from about 1.2 to 1.7 mg of AIBN/g DMA are mixed at about 25° C. in an Erlenmeyer flask and argon gas is bubbled through the solution for about 20 minutes. DMA polymerization is initiated as described above and is allowed to continue for about 15 minutes. The resulting polymers may be isolated as described above and lyophilized to yield a PDMA product with a Mw of from about 81,000 to about 112,000 Da.

Those skilled in the art will, of course, recognize that the PDMA Mw can be controlled by conventional methods, e.g., substituting with another chain transfer agent, such as n-butanol or isopropanol, with a different chain transfer constant to monomer and/or varying the amount of chain transfer agent present. In particular, the Mw can be increased by decreasing the initiator concentration relative to the starting monomer concentration and/or decreasing the amount of chain transfer agent present, or even eliminating the chain transfer agent entirely.

The Mw of the PDMA backbone can vary widely. In one embodiment, the Mw of the PDMA backbone is from about 50,000 Da to less than about 3 MDa when the PDMA is prepared by solution-polymerization. In another embodiment, the Mw of a solution-polymerized PDMA is from about 75,000 Da to about 2 MDa. As the target PDMA Mw increases, e.g., beginning at about 2 MDa and higher, the difficulty of solution-polymerization increases greatly because the solution becomes excessively viscous which may lead to problems with, e.g., homogeneity, poor heat transfer and ease of mixing. For PDMAs having a Mw greater than about 3 MDa, other methods, including those described below, may be more effective. As used herein, high weight-average molecular weight ("HMw") polymers and, particularly, HMw PDMA polymers, include those with a Mw of up to less than about 3 MDa. As used herein, ultra-high weight-average molecular weight ("UHMw") polymers and, particularly, UHMw PDMA polymers, includes those with a Mw of greater than 3 MDa. Thus, PDMA backbone polymers prepared by conventional solution-polymerization methods are limited to the HMw PDMAs.

5.3 Inverse Emulsion Polymerization of DMA to UHMw PDMA

Surprisingly, it has been found that UHMw PDMA may be prepared by the method of inverse emulsion polymerization ("IEP"). Many aspects of the IEP method have been described in detail by, e.g., "Inverse Emulsion (Microemulsion) Polymerization," Chapter 4 in *Radical Polymerization in Disperse Systems*, Barton et al., Ellis Horwood, N.Y., 1994, pp. 187-215; Candau et al., *J. Polym. Sci., Polym. Chem. Ed.*, 23:193-214 (1985); and Pross et al., *Polym. Int'l.*, 45:22-26 (1998). IEP is sometimes referred to as inverse microsuspension polymerization (Pross, p. 22.) or as inverse microemulsion polymerization (Barton, Id.). However, the preparation of UHMw PDMA by the IEP method has not been previously known, described or suggested.

Any suitable oil can be used to form the inverse emulsion. To produce desirable UHMw PDMA from DMA, the DMA should be present in the water phase. Without being bound by a particular theory, because DMA is partially soluble in the oils commonly used in the art as the oil phase for IEP, its oil-solubility is thought to limit the maximum molecular weight of the polymer produced when using such oils. Thus, when UHMw polymers are to be made, it is desirable that their monomer(s) be substantially insoluble in the oil selected.

For the purpose of selecting an appropriate monomer/oil combination, "oil insoluble" is defined by the following uncomplicated test. At a temperature of 20° C. throughout, 1 mL of the selected monomer or monomer mixture is placed into 6 mL of the selected oil(s) and vortex mixed for 1 minute. The mixing is stopped and the liquid is allowed to stand for 10 minutes. The monomer(s) is insoluble in the oil(s) if phase separation, e.g., translucency, cloudiness and/or separate layers, can be observed with the unaided eye after the 10 minute period. Conversely, the monomer(s) is soluble in the oil(s) if no phase separation, i.e., a clear solution, is observed.

For example, by this test DMA was determined to be soluble in each of acetonitrile, acetone, methanol, 1-decanol, ethyl ether, hexane, decane, petroleum ether (normal boiling range 35-60° C.), and petroleum special (normal boiling range 180-220° C.). Therefore, none of these materials, individually, would be a preferable oil phase for forming UHMw PDMA from DMA by IEP. However, DMA was determined to be insoluble by this test in, e.g., aliphatic hydrocarbons comprising at least about 15 carbon atoms. Alternatively, DMA was determined to be insoluble by this test in, e.g., aliphatic hydrocarbons with a normal boiling point at or above about 270° C. Exemplary hydrocarbons that are suitable oils for forming UHMw PDMA by IEP from DMA include pentadecane, hexadecane, heptadecane, white light mineral or paraffin oils, white heavy mineral or paraffin oils, and mineral or paraffin oils suitable for Nujol preparations.

DMA is also insoluble by the above test in, e.g., silicone oils, at least partially fluorinated hydrocarbons and liquid perfluoropolyethers ("PFPE"), also known as perfluoropolyalkylethers ("PFPAE").

Exemplary silicones that are conventional and suitable oils for forming UHMw PDMA by IEP from DMA include poly(dimethylsiloxane)-based oils such as DC200, DC510, DC550 and DC710, each of which may be available in various viscosity grades (e.g., from 10 cSt to 12,500 cSt for DC200) from Dow Corning and poly(methylphenylsiloxane)-based oils such as AR200, also from Dow Corning.

Exemplary at least partially fluorinated hydrocarbon liquids that are conventional and suitable oils for forming UHMw PDMA by IEP from DMA include the FLUORINERT series available from 3M, e.g., FC-40, FC-43, FC-70, FC-72, FC-77, FC-84, FC-87, FC-3283, FC-5312 and FC-5320

Exemplary liquid PFPEs that are conventional and suitable oils for forming UHMw PDMA by IEP from DMA include the DEMNUIM series available from Daikin Industries, Ltd., e.g., S-20, S-65, S-100 and S-200, the KRYTOX series available from DuPont, e.g., GPL100, GPL101, GPL102, GPL103, GPL104, GPL105, GPL106, GPL107, 143AB, 143AC and VPF1525, and the FOMBLIN Y, Z and M series available from Ausimont Montedison Group, e.g., Y04, Y06, Y25, Y-L VAC 25/6, YR, YR1500, YR1800, Z03, Z15, Z25, Z60, M03, M15, M30 and M60. As disclosed by, e.g., Hamada, *Phys. Chem. Chem. Phys.*, 2:115-122 (2000), the DEMNUIM-type PFPEs have the formula $F—[CF_2CF_2CF_2O]_n—H$, the KRYTOX-type PFPEs have the formula $F—[CF(CF_3)CF_2O]_l—H$, and the FOMBLIN-Z-type PFPEs have the formula $F—[(CF_2CF_2O)_2—(CF_2O)]_m—H$, where n, l and m are varied to give, e.g., different chain lengths and viscosities.

In one embodiment, oils for the IEP of DMA to UHMw PDMA include aliphatic hydrocarbons comprising at least about 15 carbon atoms, aliphatic hydrocarbons with a normal boiling point at or above about 270° C., silicone oils, at least partially fluorinated hydrocarbons, liquid perfluoropolyethers, or a mixture thereof. In another embodiment, oils for the IEP of DMA to UHMw PDMA include pentadecane, hexadecane, heptadecane, white light mineral oils, white heavy mineral oils, and mineral oils suitable for Nujol preparations. In another embodiment, the oil used for the IEP of DMA to UHMw PDMA is a mineral oil suitable for Nujol preparations.

At least one surfactant is used to form the inverse emulsion. When a plurality of surfactants is present, the additional surfactant(s) is sometimes known as a cosurfactant. It is conventional to characterize a surfactant by its hydrophilic lipophilic balance ("HLB"), a measure of the relative simultaneous attraction of the surfactant for water and oil. On the HLB scale ranging from 1 to 40, relatively lipophilic surfactants have a low numerical value while relatively hydrophylic surfactants have a high numerical value.

A wide variety of surfactants are known to be available, for example, many are listed with HLB values in *McCutcheon's Emulsifiers & Detergents*, North American Ed., Manufacturing Confectioner Pub. Co., Glen Rock, N.J., 1988, pp. 1-217. The surfactant may be nonionic or have an anionic charge, cationic charge, or both, e.g., an amphoteric surfactant, where each charge has associated with it a suitable counterion; numerous examples of each are known in the art. See Lynn, Jr. et al., "Surfactants" in *Kirk-Othmer Encyc. of Chem. Technol.*, 4th Ed., John Wiley & Sons, New York, 1997, Vol. 23, pp. 483-541.

Suitable types of nonionic surfactants are known in the art and include polyoxyethylene surfactants, e.g., alcohol ethoxylates and alkylphenol ethoxylates; carboxylic acid esters, e.g., glycerol esters and polyoxyethylene esters; anhydrosorbitol esters, e.g., mono-, di- and tri-esters of sorbitan and fatty acids; polyalkylene oxide block copolymers; and poly(oxyethylene-co-oxypropylene) nonionic surfactants. Id., pp. 506-523.

Suitable types of anionic surfactants are known in the art and include carboxylates, e.g., soaps, polyalkoxycarboxylates and N-acylsarcosinates; sulfonates, e.g., alkylbenzene sulfonates, naphthalene sulfonates and petroleum sulfonates; sulfates, e.g., alcohol sulfates and ethoxylated and sulfated alcohols; and phosphates, e.g., phosphate esters. Id., pp. 491-505.

Suitable types of cationic surfactants are known in the art and include amines, e.g., aliphatic mono-, di- and polyamines derived from fatty and rosin acids; and quaternary ammonium salts, e.g., dialkyldimethyl and alkyltrimethyl ammonium salts, alkylbenzyldimethyl ammonium chlorides, and alkylpyridinium halides. Id., pp. 524-530. Suitable types of amphoteric surfactants are known in the art and include alkylbetaines, amidopropylbetaines and imidazolinium derivatives. Id., pp. 530-532.

Considerations typically taken into account in selecting a suitable surfactant or surfactant blend to form an inverse emulsion are conventional and are summarized in, e.g., Griffin, "Emulsions" in *Kirk-Othmer Encyc. of Chem. Technol.*, 3rd Ed., John Wiley & Sons, New York, 1979, Vol. 8, pp. 909-919. Furthermore, it is recognized that some monomers, e.g., acrylamide, can sometimes act as a co-surfactant. Candau, p. 204; Barton, p. 191. In such cases, the overall HLB value of the emulsification system can differ from the HLB of the selected surfactant or surfactant blend. Barton, p. 191. Moreover, those in the art would recognize that particular characteristics of the inverse emulsion must be taken into account when selecting a surfactant. For example, when a fluorinated oil is used, it is desirable to also select an at least partially fluorinated surfactant. Taking such conventional factors into consideration, one of ordinary skill in the art would be able to select a wide variety of suitable surfactants, used individually or in combination, for the IEP of water-soluble monomers to form UHMw polymers and, particularly, to form UHMw PDMA from DMA by IEP.

In one embodiment, surfactants for the IEP of DMA to UHMw PDMA have an HLB of about 7 or less. In another embodiment, the surfactant HLB is about 6 or less. In another embodiment, the surfactant HLB is from about 3 to about 6. In another embodiment, surfactants for the IEP of DMA to UHMw PDMA have an HLB of from about 4 to about 6. In another embodiment, surfactants include SPAN-80 from Fluka, sorbitan monooleate thought to have the following structure:

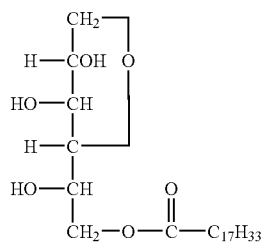

with a molecular weight of about 429 Da and an HLB of about 4.3; TETRONIC 1301 from BASF, an amine-based block copolymer nonionic surfactant thought to have the following structure:

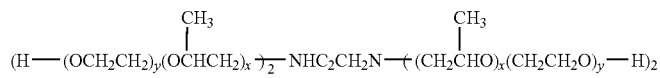

with a molecular weight of about 6,800 Da and an HLB of about 2.0; or a mixture thereof.

A sufficient amount of the surfactant is used such that a stable emulsion or microemulsion is formed; routine experimentation by one ordinarily-skilled in the art can be used to determine that amount. To obtain, after polymerization, a microemulsion of high polymer content, the ratio (by weight) of aqueous phase to oil phase is usually chosen to be as high as possible. This ratio may range, for example, from about 1:10 to about 4:1. In another embodiment, the ratio may range from about 1:2 to about 3:1. In another embodiment, the quantity of solid polymer product is greater than about 10 wt. % of the total emulsion weight.

Many types of initiators discussed above are also suitable for use in inverse emulsion polymerizations, e.g., free-radical initiators such as the azo compounds, organic peroxides and persulfates, inorganic peroxides and persulfates, and carbon-carbon initiators, as well as photoinitiators such as those described in McGinniss, "Radiation Curing" in *Kirk-Othmer Encyc. of Chem. Technol.*, 4th Ed., John Wiley & Sons, New York, 1996, Vol. 20, pp. 848-850. Polymerization may, of course, also be effected by high energy ionizing radiation sources.

In one embodiment, inverse emulsion polymerization initiators include the azo compounds, either the oil-soluble types such as AIBN or the water-soluble types such as azobutyroamidine, oil-soluble peroxides and persulfates, such as dibenzoyl peroxide, water soluble peroxides and persulfates, such as ammonium persulfate and potassium persulfate, redox initiating systems, which include the peroxy-redox types and, e.g., $K_2S_2O_8/Na_2S_2O_5$ or ferrous ammonium sulfate/ammonium persulfate, and photoinitiators, such as Michler's ketone, i.e., 4,4'-bis-(dimethylamino)benzophenone, and IRGACURE-1700 and DAROCURE-1173 from Ciba-Geigy, believed to be (25% bis(2,6-dimethoxybenzoyl)-2,4,4-trimethylpentylphosphine oxide+75% 2-hydroxy-2-methyl-1-phenyl-propan-1-one) and 2-hydroxy-2-methyl-1-phenyl-propan-1-one, respectively. In another embodiment, initiators for the IEP of DMA to UHMw PDMA include oil-soluble azo compounds, water soluble peroxides and persulfates, redox initiating systems, photoinitiators, or a mixture thereof. In another embodiment, the initiator used for the IEP of DMA to UHMw PDMA is AIBN, ammonium persulfate, potassium persulfate, Michler's ketone, 2-hydroxy-2-methyl-1-phenyl-propan-1-one, bis(2,6-dimethoxybenzoyl)-2,4,4-trimethylpentylphosphine oxide, or a mixture thereof.

The inverse emulsion and/or its aqueous phase may also contain such other additives if desired. These include chelating agents for removing polymerization inhibitors, chain transfer agents, pH adjusters, co-initiators, sensitizers, charge-transfer complexes or donor-acceptor complexes when photoinitiation is used, and other conventional additives used in their usual proportions. Polymerization in the inverse emulsion or microemulsion may be carried out by any manner known to those skilled in the art, e.g., as generally described in Griffin, pp. 919-923; U.S. Pat. No. 5,530,069 to Neff et al., at col. 3, lines 39-65 and col. 5, line 29 to col. 6, line 44; and in the references cited therein. Furthermore, the IEP of DMA to UHMw PDMA is described in Examples 6.1.1-6.1.3 herein.

The Mw of the PDMA, when it is used as poly($M_1$), can vary widely. In one embodiment, the Mw of the PDMA used as poly($M_1$) is from about 3 to about 20 MDa when UHMw PDMA is prepared by IEP. In another embodiment, the Mw of an inverse emulsion polymerized UHMw PDMA poly($M_1$) is from at least about 3 to about 10 MDa. In another embodiment, the present invention relates to the UHMw PDMA product of any of the methods herein for making it. In another embodiment, the present invention relates to the UHMw PDMA product of any of the IEP methods herein for making it.

UHMw PDMA homopolymer (non-graft copolymer), i.e., not including poly($M_2$), is also effective, e.g., in a CE separation medium for separating biomolecules. Thus, a second embodiment of the invention relates to poly(N,N-dimethylacrylamide) where the weight-average molecular weight of the poly(N,N-dimethylacrylamide) is at least about 3 MDa. In another embodiment, the sieve polymer is poly(N,N-dimethyl-acrylamide) with a weight-average molecular weight of at least about 3 MDa. In another embodiment, the UHMw PDMA has a weight-average molecular weight of from about 3 MDa to about 10 MDa. Additionally, a third embodiment of the invention relates to a method for making ultra-high molecular weight poly(N,N-dimethylacrylamide), comprising the step of polymerizing DMA in an inverse emulsion comprising an oil phase, an aqueous phase, a surfactant and an initiator, to provide poly(N,N-dimethylacrylamide) with a weight-average molecular weight of at least about 3 MDa. Another embodiment of the invention relates to the poly(N,N-dimethylacrylamide) product of this method.

5.4 Method for Making Graft Copolymer (Continued)

Once a polymeric backbone has been obtained or prepared, a pendant-forming polymerization reaction may be carried out, e.g., by free-radical grafting with monomer or monomers $M_2$ as discussed above, thereby forming a graft copolymer of the invention. Without being bound by a particular theory, a proposed mechanism for free-radical grafting of an exemplary poly($M_1$-g-$M_2$) of the invention, poly(DMA-g-AAm), is shown in the following scheme. Free-radicals 1, formed, for example, by the thermal or photolytic decomposition of a free-radical initiator at the start of polymerization, may initiate the polymerization of AAm 2 to form propagating macro-radical 3:

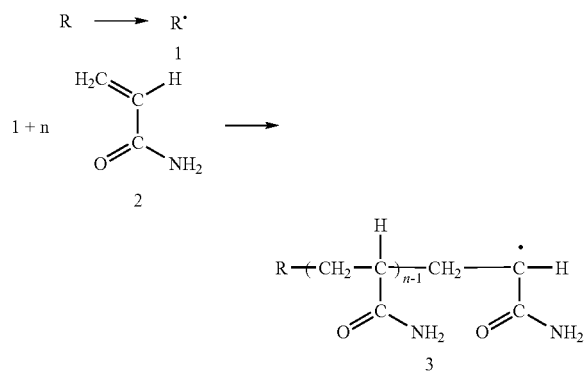

Free-radical 1 or macro-radical 3 can abstract a hydrogen atom from PDMA 4 to form macro-radicals 5 and/or 6:

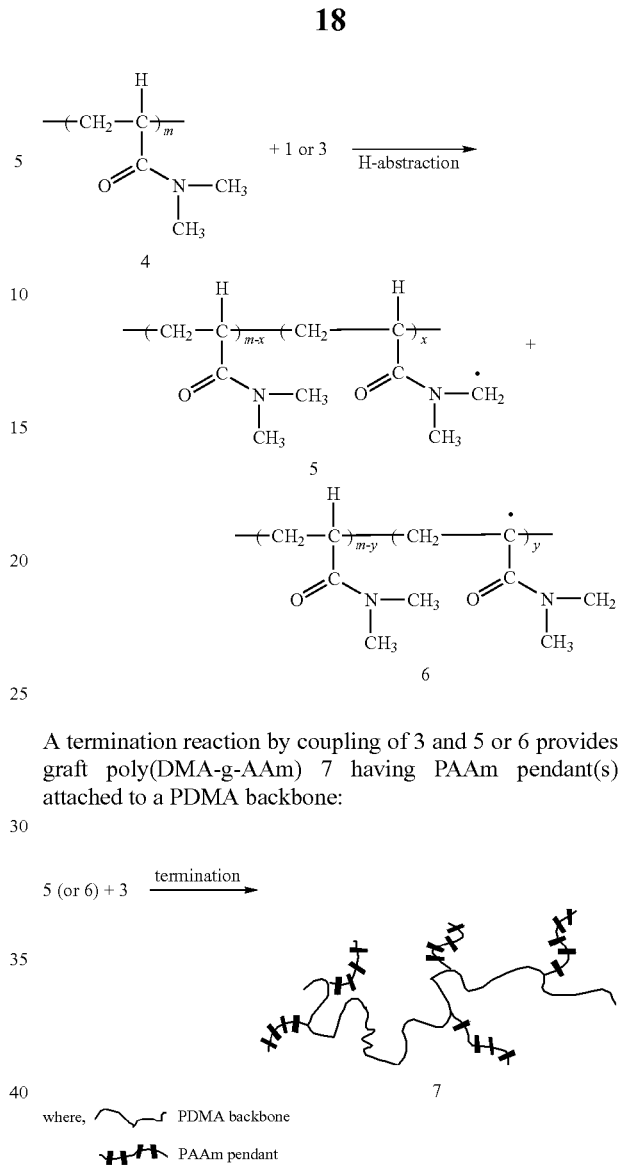

A termination reaction by coupling of 3 and 5 or 6 provides graft poly(DMA-g-AAm) 7 having PAAm pendant(s) attached to a PDMA backbone:

Alternatively, macro-radicals 5 or 6 could initiate the polymerization of AAm 2 to form a propagating PAAm pendant chain (not shown) grafted to the PDMA backbone. However, without being bound by a particular theory, it is thought that macro-radicals 5 and 6 are each ineffective as an initiator for the polymerization of 2.

Upon termination, e.g., by disproportionation, poly(DMA-g-AAm) 7 is obtained. If termination were to be by coupling between two such propagating PAAm pendant chains, crosslinking (not shown) could be expected. However, based on the results reported in Example 6.2 below for example, any substantial amount of crosslinking does not occur because the poly(DMA-g-AAm) product prepared therein is water-soluble.

A fourth embodiment of the invention relates to a method for making poly($M_1$-g-$M_2$), comprising the step of polymerizing $M_2$ in the presence of poly($M_1$) to provide poly($M_1$-g-$M_2$). It is to be understood that poly($M_1$) can be a homopolymer or a copolymer. The polymerization may be initiated by at least one free-radical, anionic and/or cationic initiator. In another embodiment, the polymerization is initiated by at least one free-radical initiator. The free-radical initiator may be dissociated thermally or photolytically in initiating the polymerization. In another embodiment, the poly($M_1$-g-$M_2$) product has a weight-average molecular weight of from about 150,000 Da to about 20 MDa. In another embodiment, the present invention relates to the poly($M_1$-g-$M_2$) product of any of the methods herein for making it.

In another embodiment of a method for making poly($M_1$-g-$M_2$), the poly($M_1$) is poly(N,N-dimethylacrylamide) and $M_2$ is acrylamide. In another embodiment, the free-radical initiator(s) are thermally or photolytically dissociated initiators selected from azo compounds, diazo compounds, organic peroxides, organic hydroperoxides, organic persulfates, organic hydropersulfates, inorganic peroxides, inorganic persulfates, peroxide-redox systems, carbon-carbon initiators, photoinitiators, or a mixture thereof. Here, the PDMA backbone can have a Mw of from about 100,000 Da to about 10 MDa. Thus, the polymeric backbone can be solution-polymerized PDMA and have a Mw of from about 500,000 Da to less than about 3 MDa, or it can be the inverse emulsion-polymerized UHMw PDMA of the invention and have a Mw of from greater than about 3 MDa to about 10 MDa.

Of course, other ways for initiating polymerization known in the art can also be used to make the poly($M_1$-g-$M_2$) of the invention. For example, exposing a combination of the poly ($M_1$) and monomer(s) to electron beams, ultraviolet radiation, usually in the presence of a photoinitiator, and high energy ionizing radiation sources, such as γ-radiation from a $^{60}$Co or $^{137}$Cs source, α-particles, β-particles, fast neutrons and x-rays, can cause the generation of free-radicals and/or ions that, in turn, initiate graft polymerization. Sanchez et al., "Initiators (Free-Radical)," at 454-457; Sheppard et al., "Initiators," in Kirk-Othmer Encyc. of Chem. Technol., 3rd Ed., John Wiley & Sons, New York, 1981, Vol. 13, pp. 367-370. At least the three following radiation grafting methods are conventional: (1) the "pre-irradiation" method, in which the backbone polymer is irradiated before interacting with the monomer(s), (2) the "mutual radiation grafting" method, in which the backbone polymer and the monomer(s) are in contact while irradiation occurs, and (3) the "peroxide" method, in which the backbone polymer is irradiated in the presence of air or oxygen before interacting with the monomer(s). Stannett et al., "Polymerization by High-Energy Radiation" in Comprehensive Polymer Science, Pergamon Press, Oxford, 1989, Vol. 4, Eastmond et al., Eds., p. 327-334. Alternatively, it is possible to synthesize graft copolymers using group-transfer polymerization. Costello, p. 359.

Another conventional method for preparing graft copolymers that can be used to prepare the poly($M_1$-g-$M_2$) of the invention is the use of telechelic polymers, also known as "macromonomers". Costello, pp. 360-361. As used herein, the term "telechelic polymer" refers to a polymer or oligomer having at least one functional end-group capable of forming bonds with another molecule. For example, a telechelic polymer consisting essentially of vinyl-terminated polymer may be suitably used. The terminal vinyl group of such a telechelic polymer can be copolymerized with a monomer or monomers, e.g., $M_1$ of the invention, to form a graft copolymer bearing, as pendant chains, the polymer of the telechelic polymer. Particularly, the telechelic polymer can be vinyl-terminated PAAm which, when copolymerized with $M_1$ of the invention, yields poly($M_1$-g-acrylamide), i.e., acrylamide as $M_2$.

Many ways of using a telechelic polymer in copolymerizations are known. For example, U.S. Pat. No. 6,214,958 B1 to Le-Khac et al., at col. 3, line 55 to col. 6, line 8, discloses several different methods for preparing copolymers comprising a polymeric backbone and pendant polymeric side-chains from one or more telechelic polymers, including using a batch process, semi-batch or semi-continuous process (i.e., two or more separate additions of monomer(s)), single stage continuous process, and multi-stage continuous process.

Alternatively, the poly($M_1$-g-$M_2$) of the present invention can be prepared from polymeric starting materials, a method that is also conventional in making graft copolymers. For example, exposure of a combination of poly($M_1$) and poly ($M_2$) to an ionizing radiation source can lead to the formation of macro-radical intermediates, e.g., by hydrogen abstraction or carbon-carbon bond cleavage. Then, the macro-radical intermediates can couple to form a single, e.g., grafted, copolymer molecule having increased molecular weight relative to the starting polymers. Adler, Science, 141:321-323 (1963); McGinniss, "Radiation Curing," in Kirk-Othmer Encyc. of Chem. Technol., 3rd Ed., John Wiley & Sons, New York, 1982, Vol. 19, p. 612. Additionally, reactive processing methods, such as reactive extrusion, can be used to make graft copolymers in situ during polymer processing operations performed with a combination of poly($M_1$) and poly($M_2$). Costello, p. 377.

5.5 Compositions of the Invention

A fifth embodiment of the invention relates to a composition comprising poly($M_1$-g-$M_2$) or a salt thereof and a buffer. The composition is useful as an electrophoresis separation medium. In one embodiment, the composition further comprises a sieve polymer or a salt thereof (described in further detail below). In another embodiment, the composition further comprises a denaturant. In the compositions, the poly ($M_1$-g-$M_2$) or a salt thereof is such that:

(a) each $M_1$ has the formula (I):

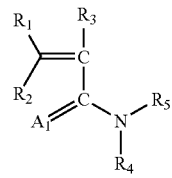

where each $A_1$ is independently O, S or $NX_1$;

each of $R_1$, $R_2$, $R_3$ and $R_4$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl) or —($C_5$-$C_{12}$ aryl)($C_1$-$C_{20}$ alkyl);

each $R_5$ is independently $C_1$-$C_{20}$ alkyl, $C_1$-$C_{20}$ heteroalkyl, $C_4$-$C_{12}$ cycloalkyl, $C_4$-$C_{12}$ heterocycloalkyl, $C_5$-$C_{12}$ aryl, $C_4$-$C_{12}$ heteroaryl, —($C_1$-$C_{20}$ alkyl)($C_4$-$C_{12}$ cycloalkyl), —($C_4$-$C_{12}$ cycloalkyl)($C_1$-$C_{20}$ alkyl), —($C_1$-$C_{20}$ heteroalkyl)($C_4$-$C_{12}$ cycloalkyl), —($C_4$-$C_{12}$ cycloalkyl)($C_1$-$C_{20}$ heteroalkyl), —($C_1$-$C_{20}$ alkyl)($C_4$-$C_{12}$ heterocycloalkyl), —($C_4$-$C_{12}$ heterocycloalkyl)($C_1$-$C_{20}$ alkyl), —($C_1$-$C_{20}$ heteroalkyl)($C_4$-$C_{12}$ heterocycloalkyl), —($C_4$-$C_{12}$ heterocycloalkyl)($C_1$-$C_{20}$ heteroalkyl), —($C_1$-$C_{20}$ alkyl)($C_5$-$C_{12}$ aryl), —($C_5$-$C_{12}$ aryl)($C_1$-$C_{20}$ alkyl), —($C_1$-$C_{20}$ heteroalkyl)($C_5$-$C_{12}$ aryl), —($C_5$-$C_{12}$ aryl)($C_1$-$C_{20}$ heteroalkyl), —($C_1$-$C_{20}$ alkyl)($C_4$-$C_{12}$ heteroaryl), —($C_4$-$C_{12}$ heteroaryl)($C_1$-$C_{20}$ alkyl), —($C_1$-$C_{20}$ heteroalkyl)($C_4$-$C_{12}$ heteroaryl), —($C_4$-$C_{12}$ heteroaryl)($C_1$-$C_{20}$ heteroalkyl), —($C_1$-$C_4$ alkyl)$_q$NH$_2$, —($C_1$-$C_4$ alkyl)$_q$CONH$_2$, —($C_1$-$C_4$ alkyl) NHCONH$_2$, —($C_1$-$C_4$ alkyl)NHCOH or —($C_1$-$C_4$ alkyl)$_q$NHCOCH$_3$, where each q is 0 or 1; and each $X_1$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl), —($C_5$-$C_{12}$ aryl)($C_1$-$C_{20}$ alkyl), —($C_1$-$C_4$ alkyl)$_q$NH$_2$, —($C_1$-$C_4$ alkyl)$_q$CONH$_2$, —($C_1$-

$C_4$ alkyl)$NHCONH_2$, —($C_1$-$C_4$ alkyl)$_q$NHCOH or —($C_1$-$C_4$ alkyl)$_q$NHCOCH$_3$, where each q is 0 or 1;
(b) each $M_2$ has the formula (II):

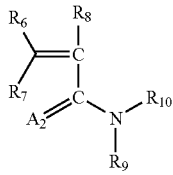

where each $A_2$ is independently O, S or $NX_2$;
each of $R_6$, $R_7$, $R_8$ and $R_9$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl) or —($C_5$-$C_{12}$ aryl)($C_1$-$C_{20}$ alkyl);
each $R_{10}$ is independently H, $C_1$-$C_{20}$ alkyl, $C_1$-$C_{20}$ heteroalkyl, $C_4$-$C_{12}$ cycloalkyl, $C_4$-$C_{12}$ heterocycloalkyl, $C_5$-$C_{12}$ aryl, $C_4$-$C_{12}$ heteroaryl, —($C_1$-$C_{20}$ alkyl)($C_4$-$C_{12}$ cycloalkyl), —($C_4$-$C_{12}$ cycloalkyl)($C_1$-$C_{20}$ alkyl), —($C_1$-$C_{20}$ heteroalkyl)($C_4$-$C_{12}$ cycloalkyl), —($C_4$-$C_{12}$ cycloalkyl)($C_1$-$C_{20}$ heteroalkyl), —($C_1$-$C_{20}$ alkyl)($C_4$-$C_{12}$ heterocycloalkyl), —($C_4$-$C_{12}$ heterocycloalkyl)($C_1$-$C_{20}$ alkyl), —($C_1$-$C_{20}$ heteroalkyl)($C_4$-$C_{12}$ heterocycloalkyl), —($C_4$-$C_{12}$ heterocycloalkyl)($C_1$-$C_{20}$ heteroalkyl), —($C_1$-$C_{20}$ alkyl)($C_5$-$C_{12}$ aryl), —($C_5$-$C_{12}$ aryl)($C_1$-$C_{20}$ alkyl), —($C_1$-$C_{20}$ heteroalkyl)($C_5$-$C_{12}$ aryl), —($C_5$-$C_{12}$ aryl)($C_1$-$C_{20}$ heteroalkyl), —($C_1$-$C_{20}$ alkyl)($C_4$-$C_{12}$ heteroaryl), —($C_4$-$C_{12}$ heteroaryl)($C_1$-$C_{20}$ alkyl), —($C_1$-$C_{20}$ heteroalkyl)($C_4$-$C_{12}$ heteroaryl), —($C_4$-$C_{12}$ heteroaryl)($C_1$-$C_{20}$ heteroalkyl), —($C_1$-$C_4$ alkyl)$_q$NH$_2$, —($C_1$-$C_4$ alkyl)$_q$CONH$_2$, —($C_1$-$C_4$ alkyl)NHCONH$_2$, —($C_1$-$C_4$ alkyl)NHCOH or —($C_1$-$C_4$ alkyl)$_q$NHCOCH$_3$, where each q is 0 or 1; and
each $X_2$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl), —($C_5$-$C_{12}$ aryl)($C_1$-$C_{20}$ alkyl), —($C_1$-$C_4$ alkyl)$_q$NH$_2$, —($C_1$-$C_4$ alkyl)$_q$CONH$_2$, —($C_1$-$C_4$ alkyl)NHCONH$_2$, —($C_1$-$C_4$ alkyl)$_q$NHCOH or —($C_1$-$C_4$ alkyl)$_q$NHCOCH$_3$, where each q is 0 or 1;
(c) provided that at least one $M_1$ is different from at least one $M_2$.

In another embodiment, $M_1$ is N-adamantyl-acrylamide, N-butoxymethyl-acrylamide, N-butyl-acrylamide, N-cyclohexyl-acrylamide, N,N-dibutyl-acrylamide, N-3-di(butyl)aminopropyl-acrylamide, N,N-diethyl-acrylamide, N-4,4-dimethoxybutyl-acrylamide, N,N-dimethyl-acrylamide, N-3-(dimethylamino)-propyl-acrylamide, N,N-dipropyl-acrylamide, N-dodecyl-acrylamide, N-2-ethylhexyl-acrylamide, N-isobornyl-acrylamide, N-methyl-acrylamide, N-methyl-, N-2,2-dimethoxyethyl-acrylamide, N-morpholinoethyl-acrylamide, N-octadecyl-acrylamide, N-propyl-acrylamide, N-3-(trimethylammonium)-propyl-acrylamide chloride, N-1,1,3-trimethylbutyl-acrylamide, N-adamantyl-methacrylamide, N-butoxymethyl-methacrylamide, N-butyl-methacrylamide, N-cyclohexyl-methacrylamide, N,N-dibutyl-methacrylamide, N-3-di(butyl)aminopropyl-methacrylamide, N,N-diethyl-methacrylamide, N-4,4-dimethoxybutyl-methacrylamide, N,N-dimethyl-methacrylamide, N-3-(dimethylamino)-propyl-methacrylamide, N,N-dipropyl-methacrylamide, N-dodecyl-methacrylamide, N-2-ethylhexyl-methacrylamide, N-isobornyl-methacrylamide, N-methyl-methacrylamide, N-methyl-, N-2,2-dimethoxyethyl-methacrylamide, N-morpholinoethyl-methacrylamide, N-octadecyl-methacrylamide, N-propyl-methacrylamide, N-3-(trimethylammonium)-propyl-methacrylamide chloride, N-1,1,3-trimethylbutyl-methacrylamide, or a mixture thereof.

In another embodiment, $M_2$ is acrylamide, N-acetyl-acrylamide, N-butoxymethyl-acrylamide, N-4,4-dimethoxybutyl-acrylamide, N-2,2-dimethoxyethyl-acrylamide, N-2-glycolic acid methyl ester acrylamide, N-2-hydroxyethyl-acrylamide, N-hydroxymethyl-acrylamide, N-methoxymethyl-acrylamide, N-3-methoxypropyl-acrylamide, N-methyl-acrylamide, N-methyl-, N-2,2-dimethoxyethyl-acrylamide, N-morpholinoethyl-acrylamide, N-2,2,2-trichloro-1-hydroxyethyl-acrylamide, N-tri(hydroxymethyl)-methyl-acrylamide, methacrylamide, N-acetyl-methacrylamide, N-butoxymethyl-methacrylamide, N-4,4-dimethoxybutyl-methacrylamide, N-2,2-dimethoxyethyl-methacrylamide, N-2-glycolic acid methyl ester methacrylamide, N-2-hydroxyethyl-methacrylamide, N-hydroxymethyl-methacrylamide, N-methoxymethyl-methacrylamide, N-3-methoxypropyl-methacrylamide, N-methyl-methacrylamide, N-methyl-, N-2,2-dimethoxyethyl-methacrylamide, N-morpholinoethyl-methacrylamide, N-2,2,2-trichloro-1-hydroxyethyl-methacrylamide, N-tri(hydroxymethyl)-methyl-methacrylamide, or a mixture thereof.

Without being bound by a particular theory, the effectiveness of the compositions of the invention is thought to arise from their ability to suppress or eliminate EOF in CE.

The weight fraction of poly($M_1$-g-$M_2$) present in a composition of the invention, based on the total weight of composition, is from about 0.0001 to about 0.02. In another embodiment, the weight fraction of poly($M_1$-g-$M_2$) present in a composition of the invention is from about 0.001 to about 0.015. In another embodiment, the weight fraction of poly ($M_1$-g-$M_2$) present in a composition of the invention is from about 0.001 to about 0.005.

5.5.1 Buffer

The present compositions comprise an buffer system for controlling pH. In one embodiment, the buffer is an aqueous buffer. In another embodiment, the buffer is a substantially dry buffer. In another embodiment, the buffer is a dry buffer. In another embodiment, the buffer provides a buffered composition with a pH of from about 5 to about 11. In another embodiment, the buffer provides a buffered composition with a pH of from about 7 to about 10. Exemplary aqueous buffers include aqueous solutions of organic acids, such as citric, acetic or formic acid; zwitterionics, such as N-tris(hydroxymethyl)-2-aminoethane sulfonic acid ("TES"), N,N-bis(2-hydroxyethyl)glycine ("BICINE"), 2-(2-amino-2-oxoethyl)-amino)ethane sulfonic acid ("ACES") or glycylglycine; inorganic acids, such as phosphoric acid; and organic bases, such as 2-amino-2-(hydroxymethyl)-1,3-propanediol ("TRIS"). Exemplary substantially dry buffers can be prepared from each of the above aqueous buffers by substantially evaporating the water. Exemplary dry buffers can be prepared from each of the above aqueous buffers by completely evaporating the water.

Buffer concentration can vary widely, for example from about 1 mmol to about 1 mol, and often about 20 mmol/liter of water is suitable. Exemplary buffer solutions for conventional CE applications include the following: 0.1 M TRIS, 0.25 M boric acid, 7 M urea with a pH of about 7.6 for single stranded polynucleotide separations; or 0.089 M TRIS, 0.089 M boric acid, 0.005 M ethylenediamine tetraacetic acid ("EDTA") for double stranded polynucleotide separations.

In another embodiment, the buffers include "GA" buffer, "TTE" buffer, or a mixture thereof. GA buffer comprises 3-((2-hydroxy-1,1-bis(hydroxymethyl)ethyl))-amino)-1- propanesulfonic acid sodium salt ("TAPS") and EDTA with from about 1 to about 4 mM of EDTA present per 100 mM of TAPS such that the pH of the buffer is about 8.0. TTE buffer comprises TRIS, TAPS and EDTA with about 1 mM of EDTA present per 50 mM of TRIS plus 50 mM of TAPS such that the pH of the buffer is about 8.4.

An effective concentration of aqueous buffer present in a composition of the invention is from about 10 mM to about 300 mM. In one embodiment, the effective concentration of aqueous buffer is from about 25 mM to about 200 mM. In another embodiment, the concentration of aqueous buffer present in a composition of the invention is from about 50 mM to about 100 mM.

5.5.2 Sieve Polymer

Optionally, the present compositions comprise a sieve polymer. In another embodiment, the present compositions comprise a sieve polymer. In CE, it is postulated that a primary mechanism of separation for different sized biomolecules, e.g., polynucleotides, is grounded on their charge-to-frictional drag ratio. Thus, it is desirable that a sieve polymer is present if, in the absence of the same, two or more biomolecules would co-migrate in CE, i.e., move with about the same mobility. For the purposes of this application, a "sieve polymer" means a polymer present in an amount effective to cause at least two components of a sample mixture to migrate with different mobilities in CE.

Gelled or crosslinked polymers can be useful sieve polymers. In another embodiment, non-covalently-crosslinked sieve polymers are used, comprising hydroxyalkylcellulose, agarose, cellulose acetate, essentially linear PAAm and the like, as disclosed by, e.g., Bode, *Anal. Biochem.*, 83:204-210 (1977); Bode, *Anal. Biochem.*, 83:364-371 (1977); Bode, *Anal. Biochem.*, 92:99-110 (1979); Hjerten et al., *J. Liquid Chromatography*, 12:2471-2477 (1989); U.S. Pat. No. 5,126, 021 to Grossman; and Tietz et al., *Electrophoresis*, 13:614-616 (1992).

When present in the compositions of the invention in one embodiment, the sieve polymer is one or more substantially uncrosslinked polymers. In another embodiment, the sieve polymer is one or more substantially linear polymers.

In another embodiment, the sieve polymer is water soluble at atmospheric pressure, a concentration of from about 0.01 to about 1 wt. %, and from about 20° C. to about 70° C., e.g., at 25° C.

In one embodiment, when a sieve polymer is present in the compositions of the invention, the sieve polymer has a weight-average molecular weight of from about 100,000 Da to about 5 MDa. In another embodiment, the sieve polymer has a weight-average molecular weight of from about 500, 000 Da to about 2 MDa. In another embodiment, the sieve polymer, when present, has a Mw of from about 800,000 Da to about 2 MDa.

In one embodiment, the sieve polymer comprises a monomer unit that is acrylamide, N-acetyl-acrylamide, N-2-cyanoethyl-acrylamide, N,N-1,2-dihydroxyethylene-bis-acrylamide, N-4,4-dimethoxybutyl-acrylamide, N-2,2-dimethoxyethyl-acrylamide, N,N-dimethyl-acrylamide, N-2-glycolic acid methyl ester acrylamide, N-2-hydroxyethyl-acrylamide, N-hydroxymethyl-acrylamide, N-methoxymethyl-acrylamide, N-3-methoxypropyl-acrylamide, N-methyl-acrylamide, N-methyl-, N-2,2-dimethoxyethyl-acrylamide, N-morpholinoethyl-acrylamide, N-2,2,2-trichloro-1-hydroxyethyl-acrylamide, N-tri(hydroxymethyl)-methyl-acrylamide, methacrylamide, N-acetyl-methacrylamide, N-2-cyanoethyl-methacrylamide, N,N-1,2-dihydroxyethylene-bis-methacrylamide, N-4,4-dimethoxybutyl-methacrylamide, N-2,2-dimethoxyethyl-methacrylamide, N,N-dimethyl-methacrylamide, N-2-glycolic acid methyl ester methacrylamide, N-2-hydroxyethyl-methacrylamide, N-hydroxymethyl-methacrylamide, N-methoxymethyl-methacrylamide, N-3-methoxypropyl-methacrylamide, N-methyl-methacrylamide, N-methyl-, N-2,2-dimethoxyethyl-methacrylamide, N-morpholinoethyl-methacrylamide, N-2, 2,2-trichloro-1-hydroxyethyl-methacrylamide, N-tri (hydroxymethyl)-methyl-methacrylamide, or a mixture thereof.

In addition, the sieve polymer can comprise or is poly (hydroxymethylene), poly(oxyethylene), poly(oxypropylene), poly(oxyethylene-co-oxypropylene), poly(vinyl alcohol), poly(vinylpyrrolidone), poly(2-ethyl-2-oxazoline), poly(2-methyl-2-oxazoline), poly((2-ethyl-2-oxazoline)-co-(2-methyl-2-oxazoline)), poly(N-acetamidoacrylamide), poly(acryloxylurea), a water-soluble polysaccharide such as hydroxyethyl cellulose or hydroxymethyl cellulose, or a mixture thereof.

In one embodiment, the sieve polymer includes an acrylamide monomer unit. In another embodiment, at least about 80 mol % of the sieve polymer's monomer units are acrylamide. In another embodiment, at least about 90 mol % of the sieve polymer's monomer units are acrylamide. In another embodiment, at least about 95 mol % of the sieve polymer's monomer units are acrylamide. In another embodiment, the sieve polymer is poly(acrylamide) that is substantially linear, i.e., in which there is an insignificant amount of branching.

In one embodiment, the sieve polymer includes a N,N-dimethylacrylamide monomer unit. In another embodiment, at least about 80 mol % of the sieve polymer's monomer units are N,N-dimethylacrylamide. In another embodiment, at least about 90 mol % of the sieve polymer's monomer units are N,N-dimethylacrylamide. In another embodiment, at least about 95 mol % of the sieve polymer's monomer units are N,N-dimethylacrylamide. In another embodiment, the sieve polymer is poly(N,N-dimethylacrylamide) that has a weight-average molecular weight of at least about 3 MDaltons.

When present, the weight fraction of sieve polymer in a composition of the invention, based on the total weight of all of the ingredients present in the composition, is from about 0.001 to about 0.1. In another embodiment, the weight fraction of sieve polymer in a composition of the invention is from about 0.005 to about 0.05. In another embodiment, the weight fraction of sieve polymer present in a composition of the invention is from about 0.01 to about 0.03 (0.01 wt. fraction=1 wt. %).

5.5.3 Denaturant

Additional optional components, such as denaturants, can be included in the present compositions, e.g., when it is desirable to prevent the formation of duplexes or secondary structures in polynucleotides. In one embodiment, denaturants include formamide, urea, detergents such as sodium dodecyl sulfate, and commercially available lactams, such as pyrrolidone and N-methylpyrrolidone, as well as their mixtures. The use of denaturants in electrophoresis is conventional and is described in, e.g., recognized molecular biology references such as Sambrook et al., *Molecular Cloning: A Laboratory Manual*, 2nd Ed. (Cold Spring Harbor Laboratory, New York, 1989). In another embodiment, the denaturant, when present, is formamide, urea, pyrrolidone, N-methylpyrrolidone or a mixture thereof. In another embodiment, the denaturant, when present, is urea. In another embodiment, the denaturant, when present, is formamide.

When present, the concentration of denaturant in a composition of the invention is from about 0.5 M to about 8 M. In another embodiment, the concentration of denaturant is from about 2 M to about 8 M. In another embodiment, the concentration of denaturant present in a composition of the invention is from about 6 M to about 8 M. A sixth embodiment of the invention relates to a composition comprising UHMw PDMA and a buffer. The composition is useful as an electrophoresis separation medium. In one embodiment, the composition further comprises a sieve polymer or a salt thereof. In another embodiment, the composition further comprises a denaturant.

The weight fraction of UHMw PDMA present in a composition of the invention, based on the total weight of all of the ingredients present in the composition, is from about 0.0001 to about 0.02. In another embodiment, the weight fraction of UHMw PDMA present is from about 0.001 to about 0.015. In another embodiment, the weight fraction of UHMw PDMA present in a composition of the invention is from about 0.001 to about 0.005. The amounts of buffer, sieve polymer when it is present, and denaturant when it is present, are as given above.

5.6 Methods for Making Compositions

A seventh embodiment of the invention relates to a method for making a composition from the poly($M_1$-g-$M_2$), described in detail above, and comprises contacting the poly($M_1$-g-$M_2$) or a salt thereof with an aqueous buffer, optionally also contacting with a sieve polymer or a salt thereof and/or a denaturant. The composition is useful as an electrophoresis separation medium. For example, the composition may be prepared by dissolving, at 25° C., the polymeric components, including the poly($M_1$-g-$M_2$) or salt thereof and, when it is present, the sieve polymer or salt thereof, in water followed by adding a concentrated form of the buffer. Alternatively, the poly($M_1$-g-$M_2$) or salt thereof can be dissolved directly in the aqueous buffer and the optional sieve polymer added to that solution. The denaturant can be present either before or after the optional sieve polymer is added. Thus, the poly($M_1$-g-$M_2$), and the sieve polymer when it is present, can be added to water, aqueous buffer, water plus denaturant, or aqueous buffer plus denaturant, depending on which combination is selected for use. Moreover, when the sieve polymer is present, it can be dissolved in, e.g., the buffer, before the poly($M_1$-g-$M_2$) is introduced. Any suitable order of adding the components for making such a composition comprising poly($M_1$-g-$M_2$) is within the scope of this embodiment of the invention.

An eighth embodiment of the invention relates to a method for making a composition from the UHMw PDMA, described in detail above, and comprises contacting the UHMw PDMA with an aqueous buffer, optionally also contacting with a sieve polymer or a salt thereof and/or a denaturant. The composition is useful as an electrophoresis separation medium. As previously discussed regarding the method for making a composition comprising poly($M_1$-g-$M_2$), the order in which the contact occurs when making a composition if the invention from UHMw PDMA is not critical. Thus, any order of adding the components for making such a composition from UHMw PDMA is within the scope of this embodiment of the invention.

5.7 Methods for Separating

In a ninth embodiment of the invention, the compositions of the invention are useful in a method for detecting or separating a sample or analyte, e.g., a biomolecule or mixture of biomolecules. As used herein, "analyte" includes the substance for which a particular sample is being tested, e.g., for the presence and/or amount contained in the sample.

For example, a suitable method for separating a mixture of biomolecules using a composition of the invention comprises:

(a) contacting a composition comprising poly($M_1$-g-$M_2$) or a salt thereof and a buffer with a mixture comprising a biomolecule; and
(b) applying an electric field to the composition in an amount sufficient to facilitate the separation of a biomolecule from the mixture.

Another suitable method for separating a mixture of biomolecules using a composition of the invention comprises:

(a) contacting a composition comprising UHMw PDMA and a buffer with a mixture comprising a biomolecule; and
(b) applying an electric field to the composition in an amount sufficient to facilitate the separation of a biomolecule from the mixture.

In another embodiment, the composition further comprises a sieve polymer or a salt thereof. In another embodiment, the composition further comprises a denaturant. In another embodiment, the composition is in a support such as a capillary tube or column, prior to contacting with a biomolecule.

The biomolecule(s) can be a polynucleotide or polynucleotides. In one embodiment, biomolecules include proteins, glycoproteins, natural and synthetic peptides, alkaloids, polysaccharides, polynucleotides, and the like. In another embodiment, biomolecule refers to polynucleotides.

The term "polynucleotide," as used herein, refers to a linear polymer of natural or modified nucleoside monomers, including double and single stranded deoxyribonucleosides, ribonucleosides, α-anomeric forms thereof, and the like. Usually the nucleoside monomers are linked by phosphodiester bonds or analogs thereof to form polynucleotides ranging in size from a few monomeric units, e.g., from about 8 to about 40, to several thousands of monomeric units. Whenever a polynucleotide is represented by a sequence of letters, such as "GTTACTG," it will be understood that the nucleotides are in 5' 3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoroselenoate, phosphorodiselenoate, phosphoroanilothioate, phosphoranilidate, phosphoramidate, and the like.

As used herein, "nucleoside" includes the natural nucleosides, including 2'-deoxy and 2'-hydroxyl forms, e.g., as described in Kornberg and Baker, *DNA Replication*, 2nd Ed. (Freeman, San Francisco, 1992). "Analogs" in reference to nucleosides includes synthetic nucleosides having modified base moieties and/or modified sugar moieties, e.g., described generally by Scheit, *Nucleotide Analogs* (John Wiley, New York, 1980).

Regarding the degree of separation of a sample or analyte, it is conventional in CE that "resolution" or "Rs" is defined as:

$$Rs=0.59(X_2-X_1)/\text{FWHM} \tag{1}$$

where $X_1$ and $X_2$ are the centers of two adjacent CE peaks and FWHM is the peak width at half-height, assuming that both peaks have substantially the same width. (See, e.g., Albarghouthi, *Electrophoresis*, 21:4096-4111 (2000)). As used herein, "crossover" is the base pair whose ($X_2-X_1$) value is equal to its FWHM value. In other words, a crossover of 650 base pairs ("bp") means that the resolution of the 650th base pair is 0.59.

In one embodiment, a method for separating a mixture of biomolecules using a composition of the invention has a crossover of at least 400 bp. In another embodiment, a method for separating a mixture of biomolecules using a composition of the invention has a crossover of at least about 600 bp. In another embodiment, a method for separating a mixture of biomolecules using a composition of the invention has a crossover of at least about 700 bp. In another embodiment, a method for separating a mixture of biomolecules using a composition of the invention has a crossover of at least about 800 bp. In another embodiment, a method for separating a mixture of biomolecules using a composition of the invention has a crossover of at least about 900 bp. In another embodiment, a method for separating a mixture of biomolecules using a composition of the invention has a crossover of at least about 1000 bp. In another embodiment, a method for separating a mixture of biomolecules using a composition of the invention has a crossover of at least about 1100 bp. In another embodiment, a method for separating a mixture of biomolecules using a composition of the invention has a crossover of at least about 1200 bp.

Certain comparative separation media are known to undergo, disadvantageously, phase separation upon storage to yield two layers. Even remixing such phase-separated comparative separation media by either shaking, tumbling or vigorous mechanical stirring can result in, e.g., significantly decreased crossover values when compared with their pre-storage CE performance. However, it has been found that the storage stability of an electrophoresis separation medium can be improved by contacting the separation medium with an effective amount of the poly($M_1$-g-$M_2$) of the invention. The weight fraction of poly($M_1$-g-$M_2$) added to a phase-separated composition, based on the total weight of all of the ingredients present in the composition before the poly($M_1$-g-$M_2$) is added, is from about 0.0001 to about 0.02, e.g., adding 0.18 wt % of GC1 (as described in Example 6.2) restored the CE performance of a phase-separated comparative separation medium.

In contrast to the comparative separation media, which are known, disadvantageously, to undergo phase separation under certain storage conditions, the compositions of the invention are relatively stable, e.g., showing no significant change in DNA sequencing performance after extended storage. For example, composition IC3 (as described in Example 6.3) was a water-clear solution with no phase separation at the time of its preparation and evaluation for DNA sequencing performance using CE. After aging for 3 months, the IC3 composition remained a water-clear solution and no phase separation was observed. The after-aging CE performance of IC3 was not significantly different from the same composition evaluated shortly after its preparation. Additionally, the after-aging CE performance results of IC3 were highly reproducible over a number of runs. Furthermore, after aging for 6 months, composition IC2 (as described in Example 6.3) remained a water-clear solution and no phase separation was observed. The after-aging CE performance of IC2 was improved, i.e., yielding a higher crossover at a lower run time, when compared with the already good CE performance of the same composition evaluated shortly after its preparation.

5.8 Electrophoresis Apparatus

A suitable electrophoresis apparatus comprises a support, e.g., a capillary, for a composition of the invention. In one embodiment, the support defines an elongate channel connectable at opposite ends to opposing polarity terminals of a voltage source and suitable for containing a composition of the invention, e.g., a separation medium. The term "capillary," as used herein, refers to a tube or channel or other structure capable of supporting a volume of composition of the invention for carrying out electrophoresis. The geometry of a support or capillary may vary widely and includes tubes with circular, rectangular or square cross-sections, channels, groves, plates, and the like, each of which may be fabricated by a wide range of technologies. For example, the support can comprise a CE array of bundled capillary channels. Alternately, the support can be of the microfabricated type, such as a channel chemically etched into a glass wafer as described by, e.g., Liu et al., *Anal. Chem.*, 71:566-573 (1999). Exemplary references describing CE microchip apparatuses include the previous citation and Woolley et al., *Anal. Chem.*, 67:3676-3680 (1995), which discloses a CE microchip with a plurality of support channels, each measuring 50 μm wide and 8 μm deep.

An important feature of a support suitable for use with the composition of the invention is the surface area-to-volume ratio of the support's inner surface in contact with the volume of the composition of the invention. High values of this ratio permit better heat transfer from the composition during electrophoresis. In one embodiment, values in the range of from about 20,000 to about 200,000 are employed. These correspond to the surface area-to-volume ratios of tubular capillaries with circular cross-sections having inside diameters of from about 200 μm to about 10 μm.

In another embodiment, the support is a tubular capillary having a length of from about 10 to about 200 cm. In another embodiment, the support is a tubular capillary having a length of less than about 100 cm. In another embodiment, the support is a tubular capillary having an inner diameter of from about 10 to about 200 μm. In another embodiment, the support is a tubular capillary having an inner diameter of from about 25 to about 75 μm.

Capillaries suitable for use with the invention may be made of silica, fused silica, silicate-based glass, such as borosilicate glass, alumina-containing glass, phosphate glass, quartz, and the like, or other silica-like materials. In one embodiment, the capillary comprises fused silica. The capillary can be uncoated on its outside surface. In another embodiment, the capillary is coated on the outside surface with a polyimide layer, e.g., to provide suitable mechanical strengthening and/or promote ease of handling. The capillary can be coated on its inside surface, with one or a plurality of layers, typically with a silane-derived coating and/or PAAm as described in, e.g., U.S. Pat. No. 4,997,537 to Karger et al., at col. 5, line 9 to col. 6, line 14. In another embodiment, the capillary is uncoated on the inside surface.

Apparatuses for performing capillary electrophoresis are well-known. Several CE instruments are commercially available, e.g., the Applied Biosystems Inc. (ABI, Foster City, Calif.) model 310 Capillary Electrophoresis Gene Analyzer. Exemplary references describing CE apparatus and their operation include Colburn et al., *Applied Biosystems Research News*, Issue 1 (Winter 1990); Grossman et al., Eds., *Capillary Electrophoresis* (Academic Press, San Diego, 1992); Harrison et al., *Science*, 261:895-897 (1993); U.S. Pat. No. 4,908,112 to Pace; U.S. Pat. No. 5,192,412 to Kambara et al.; and Seiler et al., *Anal. Chem.*, 65:1481-1488 (1993).

Contacting a composition of the invention with the support such that the support contains the composition can be performed using conventional methods, e.g., by connecting one end to a syringe and injecting the composition into the support under a controlled pressure. When the support is a capillary, the injection pressure is suitably from about 50 to about 800 psi. In another embodiment, the injection pressure for the capillary support is from about 200 to about 400 psi. Alternately, contacting a composition of the invention with the support such that the support contains the composition can be performed by connecting the capillary support to a filling tube and applying a nitrogen or helium gas pressure of from about 100 to about 500 psi for from about 5 to about 60 minutes, depending on the viscosity of the composition. U.S. Pat. No. 4,997,537 to Karger et al. discloses PAAm filling with a TEFLON tube and a syringe.

Another way for introducing a composition to the support so that the composition is contained therein is by immersing one of the two ends of the support into a reservoir containing a composition of the invention and increasing the air pressure above that composition to greater than atmospheric pressure, thereby forcing the composition into the support via positive pressure. Alternatively, the air pressure at the end of the support opposite to its immersed end may be reduced to below atmospheric, thereby drawing the composition into the support by suction.

Regardless of the method used, it is known in the art that the contained composition should fill the support substantially uniformly and homogeneously, i.e., the composition should be substantially uniform in density throughout the support and be substantially without discontinuities or voids. See, e.g., U.S. Pat. No. 5,468,365 to Menchen et al., col. 16, lines 33-45. The Brookfield viscosity of a composition of the invention is suitably from about 100 to about 1000 cPs. In another embodiment, the Brookfield viscosity of a composition of the invention is from about 200 to about 500 cPs. The compositions of the invention are appropriately characterized by Method A of the ASTM D 2196-99 test entitled "Standard Test Methods for Rheological Properties of Non-Newtonian Materials by Rotational (Brookfield type) Viscometer." In this test and by "Method A" described therein, the apparent or Brookfield viscosity is determined by experimentally measuring the torque on a spindle rotating at a constant speed within the liquid composition at a temperature of 25° C. Spindle No. 00 is used at a rotational speed of 10 rpm in a Brookfield Model RV Viscometer or its equivalent for all of these experiments.

A tenth embodiment of the invention relates to a support containing a composition of the invention. In another embodiment, the support is a capillary. In another embodiment, the capillary is a tube.

In another embodiment, when multiple CE runs are conducted for a given composition/analyte combination, the composition is substantially, i.e., 99%, removed from the capillary at the completion of each CE run and a fresh aliquot of the composition is introduced before the start of the next CE run. In another embodiment, the entire removal and filling operation is conducted under automatic control, e.g., to promote reliable and reproducible CE results.

A cathodic reservoir can contain the composition into which a cathode and the cathodic end of the capillary are immersed during electrophoresis, except for the brief period of time in which the sample is introduced. The air pressure above the composition can be finely controlled, e.g., for loading the composition into the capillary by positive pressure. An anodic reservoir can contain the composition into which an anode and the anodic end of the capillary is immersed during electrophoresis. The air pressure above that portion of the composition can also be finely controlled, if desired e.g., for drawing the composition into the capillary under reduced pressure. In another embodiment, the composition in the cathodic reservoir is substantially identical to the composition in the anodic reservoir. The entire CE apparatus is maintained at a preselected constant temperature throughout a separation run.

A high voltage source is connected between the cathode and anode such that a constant run potential in the range of from about 2 to about 60 kV is produced across the electrodes throughout CE. In another embodiment, the potential is in the range of from about 5 to about 20 kV. Alternatively, or in addition, a selected-frequency pulsed voltage may be applied between the electrodes, if desired. Currents through the capillary during the CE run are suitably in the microamp range, typically from about 2 to about 100 µA. In another embodiment, currents through the capillary during the CE run are from about 5 to about 30 µA.

A suitable sample or analyte to be analyzed using CE comprises a biomolecule or a mixture of such biomolecules. To begin a CE run, the sample may be introduced to the composition by any known means, e.g., by syringe layering injection or differential pressure. In another embodiment, the sample is introduced by electrokinetic injection, e.g., by placing the cathode and cathodic end of the capillary into a sample solution then applying an injection potential and current across the capillary for a short time. The sample is suitably electrokinetically injected for about 3 to about 150 seconds under a potential of from about 0.5 to about 18 kV. Separation commences after returning the cathode and cathodic end of the capillary into the cathode reservoir and application of the run potential and current.

An on-line detector positioned adjacent to capillary and nearer to its anodic end monitors separated bands of sample migrating through a detection zone of the capillary. Typically, an optical detection zone comprises a region of capillary in which any outer coating has been removed to permit UV and/or visible light, e.g. fluorescence, detection of the separated analyte. However, a wide variety of detection schemes are amenable for use with the invention, including UV absorbance, fluorescence emission, laser-induced fluorescence, conductance, radioactive emission, and the like. For example, detection systems for fluorescent analytes are described in U.S. Pat. No. 4,675,300 to Zare et al. and U.S. Pat. No. 4,548,498 to Folestad et al. Alternately, a 4-color detection system, such as is conventional in DNA analysis, utilizing an argon ion laser as a fluorescence-excitation light source that emits light at wavelengths of 488 and 514 nm used in conjunction with a charged coupled device detector has be described in U.S. Pat. No. 5,916,426 to Madabhushi et al.

Prior to its use with a different analyte and/or composition, the capillary may be flushed, e.g., with 20 column volumes of water, 20 column volumes tetrahydrofuran (THF), 20 column volumes 1 M NaOH and 20 column volumes of water, before it is used to contain a fresh batch of composition. In order to provide, e.g., reliable and reproducible CE results, in one embodiment the used capillary is replaced with an unused capillary containing fresh composition and the sample is introduced by electrokinetic injection, as described above.

6. EXAMPLES

As noted above, the graft copolymers and compositions and separation media containing the same; methods of making the graft copolymers and compositions and separation media containing the same; and methods of using the graft copolymers and compositions and separation media containing the same in CE yield superior CE performance in the analysis and separation of biomolecules. As also noted above, the UHMw PDMA polymers and compositions and separation media containing the same; methods of making the UHMw PDMA polymers and compositions and separation media containing the same; and methods of using the UHMw PDMA polymers and compositions and separation media containing the same in CE yield superior CE performance in the analysis and separation of biomolecules. The following examples further illustrate certain embodiments of the present invention. These examples are provided solely for illustrative purposes and in no way limit the scope of the present invention.

6.1.1 Preparation of UHMw Poly(N,N-dimethylacrylamide)

The following inverse emulsion polymerization method was used for the preparation of ultra-high molecular weight poly(N,N-dimethylacrylamide) ("PDMA").

A solution containing 12.022 g (121.28 mmol) of N,N-dimethylacrylamide (obtained from Monomer-Polymer & Dajac Laboratories, Inc., Feasterville, Pa., containing 75 ppm of 2,6-di-tert-butyl-4-methyl phenol), 4.9 mg (0.0132 mmol) of EDTA (99.999% obtained from Aldrich Chemical) and 6.1 mg (0.021 mmol) of ammonium persulfate (99.99% obtained from Aldrich Chemical) in 18.0 g of distilled water was poured into a 500 mL polypropylene beaker containing 80.0 g of mineral oil (certified for Nujol mull and obtained from Aldrich Chemical) and 4.0 g of SPAN-80. The mixture was emulsified using a 2 inch rod-shape magnetic stir bar by stirring at 2,000 rpm for 5 minutes.

The resulting milky emulsion was transferred into a 500 mL three-necked round bottom flask equipped with a mechanical stirrer having a 2 inch TEFLON stiffing blade, a water-cooled condenser, a rubber septum, a bleeding tube for bubbling and a 12 gauge syringe needle for venting. De-oxygenation of the emulsion was accomplished by bubbling in argon at 130 mL/min for 1 hour with constant stiffing at 200 rpm. Through the rubber septum, 5 µL of N,N,N',N'-tetramethylethylenediamine ("TEMED," ultra-pure grade obtained from Armesco) was added with a syringe. With constant stirring at 200 rpm, the reaction flask was then immersed into an oil bath maintained at 40±1° C. over a period of 22 hours. At the end of the reaction time, the oil bath was removed. With constant stiffing at 200 rpm, air was bubbled into the reaction mixture for 5 minutes to quench the reaction.

The product mixture was divided into four 50 mL polyethylene centrifuge tubes and each was centrifuged at 18,000 rpm and 15° C. for 30 minutes. The supernatant layer was decanted and the obtained pellets were rinsed with n-hexane to remove the mineral oil. The resulting polymer was vacuum dried at 35° C. overnight to produce 18.0 g of polymer.

To remove any residual mineral oil, a 5.6 g sample of the product was added to 150 mL of acetone and stirred to give a translucent solution. This acetone solution was poured in a fine stream into 1 L of n-hexane with vigorous stirring. The precipitated polymer was rinsed with n-hexane and vacuum dried at 40° C. for 16 hours to provide 4.6 g of PDMA, designated as UPDMA-1. The Mw of the UPDMA-1 was 8.0 MDa, as determined from batch mode MALLS testing.

6.1.2 Preparation of UHMw Poly(N,N-dimethylacrylamide)

The inverse emulsion polymerization method for the preparation of UHMw PDMA in Example 6.1.1 was carried out except for the following modifications. To 12.022 g of DMA was added a chilled solution of 4.2 mg of EDTA, 6.3 mg of ammonium persulfate and 18.0 g of distilled water with stirring. This solution was poured into a 250 mL beaker containing 80.143 g of mineral oil and 1.05 g of TETRONIC 1301. The mixture was emulsified using a 2 inch rod-shape magnetic stir bar for 10 minutes.

The resulting milky emulsion was transferred into a 250 mL three-necked round bottom flask equipped as in Example 6.1.1. De-oxygenation of the emulsion was accomplished by bubbling in water-saturated argon for 75 minutes. With constant stirring and purging with water-saturated argon at 130 mL/min, the reaction flask was then immersed into an oil bath maintained at 50±1° C. over a period of 2 hours. At the end of the reaction time, the oil bath was removed and air was bubbled into the reaction mixture to quench the reaction.

To remove the residual monomer and mineral oil, the supernatant layer was decanted, 200 mL of hexane was added, the obtained mixture was stirred vigorously for 5 minutes and then centrifuged at 1,000 rpm for 2 minutes. This procedure was repeated 3 times followed by a final decanting of the supernatant. The obtained polymer pellets were freeze-dried to provide 11.50 g of polymer.

To further remove any residual mineral oil, a 1.007 g sample of the product was added to 20 mL of acetone in a 250 mL Erlenmeyer flask, stirred and dissolved to produce a water-clear solution. This acetone solution was poured in a fine stream into 20 mL of vigorously stirred hexane to yield precipitated polymer, which was rinsed with excess hexane. The entire acetone-dissolution procedure above was then repeated. The resulting precipitated polymer was vacuum dried at 45° C. for 16 hours to produce 0.75 g of PDMA having a fibrous appearance.

For final purification, the above vacuum-dried polymer was placed in a 125 mL polypropylene beaker containing 62 g of relatively pure water obtained from a Dionics Corp. water purification system (conductivity of about 10 MΩcm), stirred and dissolved to give a water-clear solution. This solution was filtered through a 5µ ACRODISC syringe filter. The filtrate was freeze-dried as described above to produce a white polymer product having a fibrous appearance, designated as UPDMA-2. The Mw of UPDMA-2 was determined as 6.1 MDa by GPC testing.

6.1.3 Preparation of UHMw Poly(N,N-dimethylacrylamide)

The inverse emulsion polymerization method for the preparation of UHMw PDMA in Example 6.1.2 was carried out except for the following modifications. To 12.02 g of DMA was added a chilled solution of 3.7 mg of EDTA and 18.0 g of distilled water with stirring. This solution was poured into a 250 mL beaker containing 80.02 g of mineral oil and 4.01 g SPAN-80. The mixture was emulsified, transferred into a 250 mL three-necked round bottom flask equipped as in Example 6.1.1, and de-oxygenated by bubbling in water-saturated argon for 60 minutes.

To the resulting de-oxygenated emulsion was added 6.2 mg of ammonium persulfate and 4 µL TEMED. With constant stirring and purging, the reaction flask was then immersed into an oil bath maintained at 42±1° C. over a period of 22 hours.

As described in Example 6.1.1, the resulting product mixture was divided into four centrifuge tubes and each was centrifuged at 18,000 rpm and 10° C. for 30 minutes. The supernatant layer was decanted and the obtained pellets were briefly rinsed with hexane to remove the mineral oil. Then, the pellet in each centrifuge tube was redispersed with 40 mL of hexane and each dispersion was centrifuged again at 18,000 rpm and 10° C. for 30 minutes. The supernatant was decanted and the resulting polymer pellets were vacuum dried for 8 hours at 35° C.

To remove any residual mineral oil, a 3.5 g sample of the above polymer pellets was added to 75 mL of acetone and stirred to give a water-clear solution. This acetone solution was poured into 500 mL of vigorously-stirred hexane. The resulting precipitated polymer was rinsed with hexane and vacuum dried to provide PDMA having a fibrous appearance, designated as UPDMA-3. The Mw of UPDMA-3 was determined as 6.2 MDa by GPC testing (by American Polymer Standard Corporation, Mentor, Ohio).

6.2 Preparation of Poly(DMA-g-AAm) from Poly(N,N-dimethylacrylamide) and Acrylamide Poly(dimethylacrylamide-g-acrylamide) ("poly(DMA-g-AAm)") was prepared by the following representative procedure. A 500-mL three-necked round bottom flask, equipped with a mechanical stirrer, a glass bleeding tube and a syringe vent connected to an silicon oil bubbler, was charged with 250.0 g of the relatively pure water obtained from the MILLI-Q Water System (Millipore Corp., Bedford, Mass.), 7.0 g of a 28.57 wt % aqueous solution of AAm monomer, and about 2 g of dialyzed, lyophilized PDMA. The PDMA was dialyzed with 50K MWCO Spectra/Por-7 regenerated cellulose membranes for 4 days with two changes of water (5 gallons each) and lyophilized prior to its use. The PDMA weight and number-average molecular weight, as determined by GPC-MALLS was as follows: Mw=984,000 Da and Mn=315,000 Da. The amount of AAm present in the above mixture was calculated as about 2.0 g. To promote dissolution, the mixture was stirred in open air.

To the water-clear solution, 0.43 mL of an aqueous solution of 1.98 wt % ammonium persulfate (8.5 mg) was added. The mixture was purged with ultra-pure helium for 60 minutes at a flow rate of 150 mL/minute. At the end of the purging, 0.10 mL of 2-propanol was added. Table 1 summarizes the materials used. The reaction mixture was then lowered into an oil bath maintained at 50±1° C. Polymerization was conducted at that temperature over a period of 16 hours with constant stirring and under ultra-pure helium bubbling in at a rate of 100 mL/minute.

nium persulfate and the feed ratio of AAm to PDMA were varied.

While this example describes certain specific ingredients and methods, it should be recognized that satisfactory results are obtained by varying the above-described procedure, for example, by using a chain transfer agent other than 2-propanol. Additionally, combinations of chain transfer agents can used. Similarly, an initiator other than ammonium persulfate can be used or combinations of initiators can be used.

6.3 Capillary Electrophoresis of DNA Using Poly(DMA-g-AAm)

Compositions comprising the graft copolymers of the present invention were evaluated for their suitability as capillary electrophoresis separation media in DNA sequencing. In the following examples, each composition and/or separation medium was evaluated in CE by using an ABI 310 Capillary Electrophoresis Gene Analyzer equipped with a 47 cm long by 50 μm inner diameter uncoated fused silica capillary.

In each comparative separation medium, either GA buffer or TTE buffer was used. Urea denaturant was also present.

TABLE 1

Formulations used for the preparation of poly(DMA-g-AAm)

| Graft Copolymer Designation | AAm (g) | PDMA (g) | Approx. WFR* | Water (g) | 2-Propanol (mL) | Ammonium persulfate (g) | Mw (MDa) | Mn (MDa) |
|---|---|---|---|---|---|---|---|---|
| GC1 | 2.0011 | 2.0024 | 1 | 250.0 | 0.10 | 0.0085 | 1.48 | 0.47 |
| GC2 | 9.1654 | 0.9169 | 10 | 250.0 | 0.50 | 0.0396 | 2.15 | 1.02 |

*Weight Feed Ratio = (Weight monomer(s), g)/(Weight backbone polymer, g)

After 16 hours, the reaction was stopped and the reaction mixture was dialyzed as described above. After lyophilization, 3.7 g of the first graft copolymer ("GC1") was obtained (92% yield) with the following molecular weight as determined by GPC-MALLS: Mw=1,477,000 Da, Mn=471,000 Da.

A portion of this purified GC1 (1.93 g) was transferred into a Soxhlet extractor and was extracted with boiling acetone continuously for 3 days to remove any homopolymer of PDMA, which is known to be soluble in acetone. At the end of the extraction, the swollen polymer was vacuum dried for 5 hours at 40° C. to provide 1.42 g of extracted GC1 product that was, because of these extreme extraction conditions, presumably free of PDMA homopolymer. GPC-MALLS determinations showed that the extracted GC1 graft polymer had the following properties: Mw=1,422,500 Da and Mn=499,500 Da.

As illustrated in Table 1, a higher molecular weight graft copolymer 2 ("GC2") with a different AAm/PDMA ratio was prepared from the same starting materials and using the above procedure except that the amounts of 2-propanol and ammo- Each separation medium was prepared by dissolving, at 25° C., the polymeric components in the buffer plus denaturant.

CSM2 and 3 were each prepared with lyophilized, substantially linear PAAm of the following approximate molecular weight as determined by GPC-MALLS: Mw=1.5 MDa. CSM1 and 3 were each prepared with lyophilized PDMA of the following approximate molecular weight as determined by GPC-MALLS: Mw=984,000 Da.

CE sequencing runs for these comparative separation media were conducted in the presence of a ladder of TET-dye labeled fragments, having lengths of 35, 50, 75, 100, 139, 150, 160, 200, 250, 300, 340, 350, 400, 450, 490, 500, 550, 600, 650 and 700 base pairs, at several temperatures, usually 50, 60 and 70° C., with 1.5 kV injection voltage and 10 sec injection time and with 9.5 kV run voltage. The crossover and run time were determined at each temperature.

The composition and CE sequencing performance for each of these comparative separation media is summarized in Table 2.

TABLE 2

CE Crossover and Run Time of Comparative Separation Media, Average of 4 Runs

| Separation Medium Designation | Weight % | | | Urea (wt %) | Crossover (bp) | | | Run Time for 700 bp (min) | | |
|---|---|---|---|---|---|---|---|---|---|---|
| | PAAm | PDMA | Buffer | | 50° C. | 60° C. | 70° C. | 50° C. | 60° C. | 70° C. |
| CSM1 | — | 4.9 | GA | 39.2 | 532 | 495 | 412 | 92.5 | 106.2 | 137.3 |
| CSM2 | 2.28 | — | GA | 37.9 | 232 | 254 | 228 | 49.5 | 46.9 | 49.6 |

CSM1, lacking PAAm, had a low 50° C. crossover value of 532 bp and an excessive run time (92.5 min) In CSM2, PDMA or any other dynamic coating was absent. This formulation exhibited an extremely low 50° C. crossover value, 232 bp, the worst resolution of the three comparative separation media, but had a relatively short run time of 49.5 min.

Compositions of the invention were prepared from poly (DMA-g-AAm), e.g., by the method described above but also using the dialyzed, lyophilized, extracted graft copolymer of this invention. The dialysis procedure was as described above. IC1-3 were each prepared with the same PAAm used in CSM2. IC1 and 2 were each prepared with the graft copolymer GC2 described in Example 6.2 while IC3 was prepared with the acetone-extracted graft copolymer GC1 described in that example. TET-dye labeled fragment sequencing runs were conducted as described above for the CSM separation media. The composition and CE sequencing performance for each of the compositions of the invention is summarized in Table 3. In Tables 2 and 3, the weight percent values specified are based on the total weight of the composition, i.e., the separation medium.

acetone and the purified GC1 of Example 6.2 was swollen in boiling acetone for 3 days of acetone extraction in the Soxhlet extractor, an undetectable amount of PDMA remained in the extracted GC1.

The results from DNA sequencing using CE clearly distinguish among separation media containing only PAAm and those containing PDMA and PAAm. A separation medium containing PAAm as the sole polymeric component, i.e., CSM2 in Table 2 above, does not suppress EOF well enough to give a high crossover value. In contrast, the extracted copolymer products IC1-3 of Table 3, when present with PAAm in compositions of the invention used as a separation media, performed markedly better than CSM2, e.g., by effectively suppressing EOF as indicated by their high crossover values relative to CSM2. This greatly improved CE performance confirms that the PDMA reactant was chemically incorporated into the graft copolymers GC1 and GC2 present in IC1-3.

TABLE 3

CE Crossover and Run Time of Compositions of the Invention, Average of 8 Runs

| Composition | Weight % | | | | Urea | Crossover (bp) | | | Run Time for 700 bp (min) | | |
|---|---|---|---|---|---|---|---|---|---|---|---|
| Designation | PAAm | GC2 | GC1 | Buffer | (wt %) | 50° C. | 60° C. | 70° C. | 50° C. | 60° C. | 70° C. |
| IC1 | 2.02 | 0.22 | — | GA | 37.9 | 643 | 618 | 579 | 46.2 | 46.6 | 60.3 |
| IC2 | 1.52 | 0.88 | — | GA | 38.2 | 637 | 615 | 597 | 49.8 | 47.8 | 55.3 |
| IC3 | 2.21 | — | 0.20 | GA | 38.0 | 633 | 617 | 587 | 47.4 | 46.6 | 50.1 |

As illustrated in Table 3, IC1 was effective in CE. IC1 provided an improved crossover value at 50° C. of 643 bp, relative to the 532 bp of CSM1 and the 232 bp of CSM2. At 50° C., IC1 had run times shorter than CSM1 and CSM2.

As also illustrated in Table 3, decreasing the amount of PAAm (i.e., the sieve polymer) from 2.02 wt % in IC1 to 1.52 wt % in IC2, with a corresponding increase in the amount of graft copolymer from 0.22 to 0.88 wt %, respectively, also resulted in a higher 50° C. crossover value relative to, e.g., CSM1, 637 bp to 532 bp, respectively. At 50° C., IC2 also had run times shorter than or comparable to CSM1 and CSM2.

A composition of the invention comprising the lower molecular weight graft copolymer GC1, called IC3, was also effective in CE. IC3 provided an improved crossover value at 50° C. of 633 bp, relative to the 532 bp of CSM1 and the 232 bp of CSM2, also with shorter run times.

6.4 CE as a Confirmation of the Structure of the Poly(DMA-g-AAm)

Poly(DMA-g-AAm) graft copolymers of the invention were prepared using free-radical polymerization of acrylamide in an aqueous solution of PDMA, as described in Example 6.2. After dialysis and lyophilization, as also described therein, which removed unreacted acrylamide, initiator and other low molecular weight impurities, only the following polymeric products could have been present in the isolate: (1) poly(DMA-g-AAm); (2) PAAm, which is relatively acetone insoluble; and (3) unreacted PDMA, which is very acetone soluble.

As described in Example 6.2, the "purified GC1" was subjected to boiling acetone extraction to produce "extracted GC1". Such extraction was used because neither GC1 nor GC2 was soluble in acetone. Since PDMA is very soluble in 6.5 Capillary Electrophoresis of DNA Using UHMw PDMA Capillary electrophoresis separation media IC4 and IC5, each comprising an UHMw PDMA polymer of the present invention, were evaluated for their suitability for DNA sequencing.

IC4 was made from 3.6 wt % of the UPDMA-2 UHMw PDMA prepared by the procedure of Example 6.1.2. IC5 was made from 2.6 wt % of the UPDMA-3 UHMw PDMA prepared by the procedure of Example 6.1.3. GA buffer was used and 39.2 wt % of urea denaturant was also present in each of IC4 and IC5. Each of these separation media was prepared by dissolving, at 25° C., the UHMw PDMA in the buffer plus denaturant.

IC4 was evaluated for DNA sequencing performance using CE as described in Example 6.3. The results were as follows: a 50° C. crossover of 625 bp with a 76 minute run time, each from an average of 4 runs. Thus, IC4, containing UPDMA-2 and lacking PAAm, had a much higher 50° C. crossover value of 625 bp when compared with the 532 bp obtained with CSM1, containing lower molecular weight PDMA and also lacking PAAm. Additionally, the 76 minute run time for IC4 at 50° C. was, advantageously, far shorter when compared to the 92.5 minute run time of CSM1.

IC5 was also evaluated for DNA sequencing performance using CE as described in Example 6.3. The results were as follows: a 50° C. crossover of 610 bp with a 52 minute run time, each from an average of 4 runs. IC5, containing UPDMA-3, also had a much higher 50° C. crossover value of 610 bp when compared with the 532 bp obtained with CSM1, containing lower molecular weight PDMA and also lacking PAAm. Additionally, the run time for IC5, at 50° C., at 52 minutes, was also dramatically and advantageously lower when compared to the 92.5 minute run time of CSM1.

All publications and patent applications are herein incorporated by reference to the same extent as if each individual publication or patent application was specifically and individually indicated to be incorporated by reference.

All concentrations herein are by weight unless otherwise noted.

Although the invention has been described with reference to particular embodiments, it will be appreciated that various changes and modifications may be made without departing from the spirit or scope of the invention.

What is claimed is:

1. A method for separating a mixture of biomolecules, comprising:

(1) contacting a composition comprising a buffer and an effective amount of a poly($M_1$-g-$M_2$), or a salt thereof, wherein:

(a) poly($M_1$-g-$M_2$) comprises a first backbone polymer, poly ($M_1$), formed from a monomer unit $M_1$ having the formula (I):

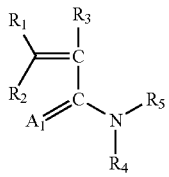

wherein each $A_1$ is independently O, S or $NX_1$;

each of $R_1$, $R_2$, $R_3$ and $R_4$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl) or —($C_5$-$C_{12}$ aryl)($C_1$-$C_{20}$ alkyl);

each $R_5$ is independently $C_1$-$C_{20}$ alkyl, $C_1$-$C_{20}$ heteroalkyl, $C_4$-$C_{12}$ cycloalkyl, $C_4$-$C_{12}$ heterocycloalkyl, $C_5$-$C_{12}$ aryl, $C_4$-$C_{12}$ heteroaryl, —($C_1$-$C_{20}$ alkyl)($C_4$-$C_{12}$ cycloalkyl), —($C_4$-$C_{12}$ cycloalkyl)($C_1$-$C_{20}$ alkyl), —($C_1$-$C_{20}$ heteroalkyl)($C_4$-$C_{12}$ cycloalkyl), —($C_4$-$C_{12}$ cycloalkyl)($C_1$-$C_{20}$ heteroalkyl), —($C_1$-$C_{20}$ alkyl)($C_4$-$C_{12}$ heterocycloalkyl), —($C_4$-$C_{12}$ heterocycloalkyl)($C_1$-$C_{20}$ alkyl), —($C_1$-$C_{20}$ heteroalkyl)($C_4$-$C_{12}$ heterocycloalkyl), —($C_4$-$C_{12}$ heterocycloalkyl)($C_1$-$C_{20}$ heteroalkyl), —($C_1$-$C_{20}$ alkyl)($C_5$-$C_{12}$ aryl), —($C_5$-$C_{12}$ aryl)($C_1$-$C_{20}$ alkyl), —($C_1$-$C_{20}$ heteroalkyl)($C_5$-$C_{12}$ aryl), —($C_5$-$C_{12}$ aryl)($C_1$-$C_{20}$ heteroalkyl), —($C_1$-$C_{20}$ alkyl)($C_4$-$C_{12}$ heteroaryl), —($C_4$-$C_{12}$ heteroaryl)($C_1$-$C_{20}$ alkyl), —($C_1$-$C_{20}$ heteroalkyl)($C_4$-$C_{12}$ heteroaryl), —($C_4$-$C_{12}$ heteroaryl)($C_1$-$C_{20}$ heteroalkyl), —($C_1$-$C_4$ alkyl)$_q$$NH_2$, —($C_1$-$C_4$ alkyl)$_q$$CONH_2$, —($C_1$-$C_4$ alkyl)$NHCONH_2$, —($C_1$-$C_4$ alkyl)$NHCOH$ or —($C_1$-$C_4$ alkyl)$_q$$NHCOCH_3$, where each q is 0 or 1; and each $X_1$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl), —($C_5$-$C_{12}$ aryl)($C_1$-$C_{20}$ alkyl), —($C_1$-$C_4$ alkyl)$_q$$NH_2$, —($C_1$-$C_4$ alkyl)$_q$$CONH_2$, —($C_1$-$C_4$ alkyl)$NHCONH_2$, —($C_1$-$C_4$ alkyl)$_q$$NHCOH$ or —($C_1$-$C_4$ alkyl)$_q$$NHCOCH_3$, where each q is 0 or 1;

(b) poly($M_1$-g-$M_2$) comprises a second pendent polymer, poly ($M_2$), grafted to poly($M_1$), wherein the pendent polymer consists of a polymer formed from monomer units $M_2$ having the formula (II):

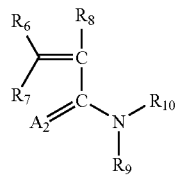

wherein each $A_2$ is independently O, S or $NX_2$;

each of $R_6$, $R_7$, $R_8$ and $R_9$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl) or —($C_5$-$C_{12}$ aryl)($C_1$-$C_{20}$ alkyl);

each $R_{10}$ is independently H, $C_1$-$C_{20}$ alkyl, $C_1$-$C_{20}$ heteroalkyl, $C_4$-$C_{12}$ cycloalkyl, $C_4$-$C_{12}$ heterocycloalkyl, $C_5$-$C_{12}$ aryl, $C_4$-$C_{12}$ heteroaryl, —($C_1$-$C_{20}$ alkyl)($C_4$-$C_{12}$ cycloalkyl), —($C_4$-$C_{12}$ cycloalkyl)($C_1$-$C_{20}$ alkyl), —($C_1$-$C_{20}$ heteroalkyl)($C_4$-$C_{12}$ cycloalkyl), —($C_4$-$C_{12}$ cycloalkyl)($C_1$-$C_{20}$ heteroalkyl), —($C_1$-$C_{20}$ alkyl)($C_4$-$C_{12}$ heterocycloalkyl), —($C_4$-$C_{12}$ heterocycloalkyl)($C_1$-$C_{20}$ alkyl), —($C_1$-$C_{20}$ heteroalkyl)($C_4$-$C_{12}$ heterocycloalkyl), —($C_4$-$C_{12}$ heterocycloalkyl)($C_1$-$C_{20}$ heteroalkyl), —($C_1$-$C_{20}$ alkyl)($C_5$-$C_{12}$ aryl), —($C_5$-$C_{12}$ aryl)($C_1$-$C_{20}$ alkyl), —($C_1$-$C_{20}$ heteroalkyl)($C_5$-$C_{12}$ aryl), —($C_5$-$C_{12}$ aryl)($C_1$-$C_{20}$ heteroalkyl), —($C_1$-$C_{20}$ alkyl)($C_4$-$C_{12}$ heteroaryl), —($C_4$-$C_{12}$ heteroaryl)($C_1$-$C_{20}$ alkyl), —($C_1$-$C_{20}$ heteroalkyl)($C_4$-$C_{12}$ heteroaryl), —($C_4$-$C_{12}$ heteroaryl)($C_1$-$C_{20}$ heteroalkyl), —($C_1$-$C_4$ alkyl)$_q$$NH_2$, —($C_1$-$C_4$ alkyl)$_q$$CONH_2$, —($C_1$-$C_4$ alkyl)$NHCONH_2$, —($C_1$-$C_4$ alkyl)$NHCOH$ or —($C_1$-$C_4$ alkyl)$_q$$NHCOCH_3$, where each q is 0 or 1; and each $X_2$ is independently H, $C_1$-$C_{20}$ alkyl, $C_4$-$C_{12}$ cycloalkyl, $C_5$-$C_{12}$ aryl, $C_4$-$C_{12}$ heteroaryl, —($C_1$-$C_{20}$ alkyl)($C_5$-$C_{12}$ aryl), —($C_5$-$C_{12}$ aryl)($C_1$-$C_{20}$ alkyl), —($C_1$-$C_4$ alkyl)$_q$$NH_2$, —($C_1$-$C_4$ alkyl)$_q$$CONH_2$, —($C_1$-$C_4$ alkyl)$NHCONH_2$, —($C_1$-$C_4$ alkyl)$_q$$NHCOH$ or —($C_1$-$C_4$ alkyl)$_q$$NHCOCH_3$, where each q is 0 or 1;

with a mixture comprising a biomolecule; and (2) applying an electric field to the composition in an amount sufficient to facilitate the separation of the biomolecule from the mixture.

2. The method of claim 1, wherein the separation is performed within a capillary tube and two or more biomolecules are polynucleotides.

3. The method of claim 2, wherein the separation has a crossover of at least 400 base pairs.

4. The method of claim 3, wherein $M_1$ is N,N-dimethylacrylamide and $M_2$ is acrylamide.

5. The method of claim 2, wherein $M_1$ is N,N-dimethylacrylamide and $M_2$ is acrylamide.

6. The method of claim 1, wherein the composition further comprises a sieve polymer.

7. The method of claim 6, wherein the sieve polymer is poly(acrylamide).

8. The method of claim 7, wherein $M_1$ is N,N-dimethylacrylamide and $M_2$ is acrylamide.

9. The method of claim 6, wherein $M_1$ is N,N-dimethylacrylamide and $M_2$ is acrylamide.

10. The method of claim 1, wherein the poly($M_1$-g-$M_2$) or a salt thereof has a weight-average molecular weight of from about 150,000 Daltons to about 20 MDaltons.

11. The method of claim 10, wherein the composition further comprises a sieve polymer or a salt thereof having a weight-average molecular weight of from about 100,000 Daltons to about 5 MDaltons.

12. The method of claim 11, wherein the sieve polymer is substantially linear poly(acrylamide).

13. The method of claim 12, wherein $M_1$ is N,N-dimethylacrylamide and $M_2$ is acrylamide.

14. The method of claim 11, wherein $M_1$ is N,N-dimethylacrylamide and $M_2$ is acrylamide.

15. The method of claim 10, wherein $M_1$ is N,N-dimethylacrylamide and $M_2$ is acrylamide.

16. The method of claim 10, wherein the sum of the weight of all $M_2$ units present in the poly($M_1$-g-$M_2$) or a salt thereof divided by the sum of the weight of all $M_1$ units present in the poly($M_1$-g-$M_2$) or a salt thereof is at least about 0.1.

17. The method of claim 1, wherein the buffer is an aqueous buffer.

18. The method of claim 17, wherein the composition has a pH of from about 5 to about 11.

19. The method of claim 18, wherein the composition further comprises formamide, urea, pyrrolidone, N-methylpyrrolidone or a mixture thereof.

20. The method of claim 18, wherein the composition further comprises urea.

21. The method of claim 18, wherein the composition further comprises formamide.

22. The method of claim 18, wherein $M_1$ is N,N-dimethylacrylamide and $M_2$ is acrylamide.

23. The method of claim 17, wherein the composition has a pH of from about 7 to about 10.

24. The method of claim 17, wherein $M_1$ is N,N-dimethylacrylamide and $M_2$ is acrylamide.

25. The method of claim 1, wherein $M_1$ is N,N-dimethylacrylamide and $M_2$ is acrylamide.

26. The method of claim 1, wherein the sum of the weight of all $M_2$ units present in the poly($M_1$-g-$M_2$) or a salt thereof divided by the sum of the weight of all $M_1$ units present in the poly($M_1$-g-$M_2$) or a salt thereof is at least about 0.1.

27. The method of claim 1, wherein the second pendent polymer, poly($M_2$), is grafted to poly($M_1$) through $R_3$, $R_5$, or $R_4$, if $R_4$ is not H.

28. The method of claim 1, wherein at least one $M_1$ is different from at least one $M_2$.

29. The method of claim 1, wherein $M_1$ is different from $M_2$.

* * * * *